(12) United States Patent
Ebisawa

(10) Patent No.: US 8,781,761 B2
(45) Date of Patent: Jul. 15, 2014

(54) ROTARY SPEED DETECTION METHOD AND DEVICE THEREFOR, REACTION LIQUID VISCOSITY DETECTION METHOD AND DEVICE THEREFOR, AND METHOD FOR MANUFACTURING REACTION PRODUCT

(75) Inventor: Shouei Ebisawa, Chiba (JP)

(73) Assignee: DIC Corporation, Tokyo (JP)

(*) Notice: Subject to any disclaimer, the term of this patent is extended or adjusted under 35 U.S.C. 154(b) by 0 days.

(21) Appl. No.: 13/823,110

(22) PCT Filed: Dec. 12, 2011

(86) PCT No.: PCT/JP2011/078673
§ 371 (c)(1),
(2), (4) Date: Mar. 14, 2013

(87) PCT Pub. No.: WO2012/090686
PCT Pub. Date: Jul. 5, 2012

(65) Prior Publication Data
US 2013/0172507 A1 Jul. 4, 2013

(30) Foreign Application Priority Data
Dec. 27, 2010 (JP) ................................ 2010-289597

(51) Int. Cl.
*G01P 3/44* (2006.01)
*G01N 11/14* (2006.01)

(52) U.S. Cl.
USPC ............................. 702/50; 701/147; 73/54.01

(58) Field of Classification Search
CPC ................................. G01N 11/14; G01P 3/44
USPC .................................... 702/50, 147; 73/54.01
See application file for complete search history.

(56) References Cited

U.S. PATENT DOCUMENTS 4,532,458 A * 7/1985 Kuznetsov et al. ............ 318/111
5,994,481 A * 11/1999 Ogura et al. ..................... 526/59
(Continued)

FOREIGN PATENT DOCUMENTS

| JP | 63-144795 | 6/1988 |
| JP | 63-249486 | 10/1988 |
| JP | 08-114613 | 5/1996 |
| JP | 2010-190882 | * 9/2010 |

OTHER PUBLICATIONS

Chalmers, et al., "General theory of solid-rotor induction machines", IEEE, 1972.*

(Continued)

*Primary Examiner* — John Breene
*Assistant Examiner* — Ruihua Zhang
(74) *Attorney, Agent, or Firm* — Jianq Chyun IP Office

(57) ABSTRACT

The method for detecting rotary speed includes: a step (I) for deeming the difference between input power (P) and loss power (A) to be a first order approximation value ($PM_1$) of the mechanical output of an induction motor, and for obtaining a first approximation value ($N_1=N_S(1-S_1)$) ($N_S$ is the synchronous speed) of the rotary speed from the functional relationship ($PM_1=\kappa S_1$) of the output (PM) and slip (S) known for the induction motor; a step (II) for obtaining loss power ($B_1$) based on the value ($N_1$); and a step (III) for deeming a second order approximation value ($PM_2$) of the motor output to be $P-(A+B_1)$, and for obtaining a second order approximation value ($N_2=N_S(1-S_2)$) of the rotary speed from the functional relationship ($PM_2=\kappa S_2$) ($\kappa$ is the motor constant) of the output (PM) and slip (S).

11 Claims, 8 Drawing Sheets

(56) References Cited

U.S. PATENT DOCUMENTS

| | | | |
|---|---|---|---|
| 6,469,469 B1* | 10/2002 | Chambers et al. | 318/801 |
| 6,828,751 B2* | 12/2004 | Sadasivam et al. | 318/729 |
| 2003/0033859 A1* | 2/2003 | Schoeb et al. | 73/54.28 |

OTHER PUBLICATIONS

Zhang, et al, "Application of a matrix converter for the power control of a variable-speed wind-turbine driving a doubly-fed induction generator", IEEE, 1997.*

Jimoh, et al., "Stray losses in induction machines: Part I, definition, origin and measurement", IEEE 1985.*

Lu, et al., "A survey of efficiency estimation methods of in-service induction motors with considerations of condition monitoring requirements", IEEE, 2005.*

"International Search Report (Form PCT/ISA/210)", published on Jan. 17, 2012, with English translation thereof, p. 1-p. 4, in which the listed references (JP2010-190882, JP63-144795, JP63-249486, JP08-114613) were cited.

* cited by examiner example in which rotary speed of reaction vessel is measured 1. rotary speed detected by employing the method of present invention 2. speed measured by using a conventional measurement instrument example in which viscosity is measured during the reaction 1. viscosity detected by employing the method of present invention (without employing a measurement instrument)

2. viscosity detected by using a speed measurement instrument

ROTARY SPEED DETECTION METHOD AND DEVICE THEREFOR, REACTION LIQUID VISCOSITY DETECTION METHOD AND DEVICE THEREFOR, AND METHOD FOR MANUFACTURING REACTION PRODUCT

CROSS-REFERENCE TO RELATED APPLICATION

This application is a 371 of international application of PCT application serial no. PCT/JP2011/078673, filed on Dec. 12, 2011, which claims the priority benefit of Japan application no. 2010-289597, filed on Dec. 27, 2010. The entirety of each of the above-mentioned patent applications is hereby incorporated by reference herein and made a part of this specification.

BACKGROUND OF THE INVENTION

1. Field of the Invention

The present invention generally relates to a rotary speed detection method of a rotating shaft of an induction motor and a detection device using the same for detecting the rotary speed of the rotating shaft of the induction motor, a rotational torque detection method of a rotating shaft of an induction motor and a detection device using the same for detecting the rotary torque of the rotating shaft of the induction motor, a reaction liquid viscosity detection method and a reaction liquid viscosity detection device and a manufacturing method of a reaction product.

2. Description of Related Art

Measuring instruments for measuring rotary speed are generally categorized into: contact type (mechanical type) and non-contact type (optical type, electromagnetic type) according to the manner of measurement, digital and analog according to the processing method of the measurement signal, and explosion-proof and non-explosion-proof according to the place of use. Particularly, in the manufacturing sites at which resins, such as urethane, varnish, phenol and the like, are manufactured via chemical reaction, using the explosion-proof measuring instruments is required.

Generally, measuring instruments of rotary speed known as the conventional ones are: handy digital tachometer which includes both contact type and non-contact type (Ono Sokki HT-5500), visible light type takohai tester (Hioki FT3405), electromagnetic rotary measuring instrument (Hioki MP-200), explosion-proof rotary measuring instrument (Ono Sokki RP-200) and the like. These measuring instruments are capable of both high accuracy and safety in use by being appropriately selected based on the type of application.

The application of these rotary speed measuring instruments is widespread, and for example, they are used to measure the rotary speed of the rotating shafts (output shafts) of induction motors.

On the other hand, the inventors of the present invention provide a reaction liquid viscosity detector (Patent Reference 1), wherein an induction motor driven by an inverter is used as a power source and the detector is installed in a reaction vessel which performs the agitating the reaction liquid by rotating a rotational shaft having an agitation blade. The detector includes the following 1) to 5) means, wherein the rotary torque is obtained by using $T=(P_I-P_L)/\omega$ based on the power input ($P_I$), the loss power ($P_L$), and the angular velocity ($\omega$) obtained from the measured values at each measuring instrument, and the detector is characterized in that the reaction liquid viscosity is calculated from the rotary torque.

1) power detection means for measuring the power supplied to the induction motor,
2) current detection means for measuring the current supplied to the induction motor,
3) voltage detection means for measuring the voltage supplied to the induction motor,
4) rotational speed detection means for measuring the speed of the rotational shaft of the induction motor, and
5) frequency detection means for measuring the inverter output frequency.

Patent reference 1: Japan Laid Open Publication No. 2010-190882

SUMMARY OF THE INVENTION

Problems that the Invention is to Solve

In the viscosity detector of Patent Reference 1, based on the measured values obtained from each abovementioned means of 1) to 5), the rotary torque of the rotating shaft of the induction motor can be detected with high accuracy, and the corresponding viscosity of the reaction liquid can be obtained with high accuracy as a result.

In the viscosity detector of Patent reference 1, the rotational speed detection means is dispensable and used as an instrument to obtain the rotational speed of the rotating shaft of the induction motor. However, the rotational speed detection means used in the manufacturing sites that deals with reaction liquid must meet the explosion-proof criteria. The rotational speed detection means which meets the explosion-proof criteria is expensive and has the disadvantages of increasing the installation cost of the viscosity detector, longer delivery period, and being hard to be popularized because the production line has to be stopped during installation. Accordingly, without using a rotational speed detector to detect the rotary speed of the rotating shaft of the induction motor is desired.

In view of the background art, without employing an existing rotary speed measurement instrument, the present invention is to provide a rotary speed detection method of the rotating shaft of the induction motor and a device thereof capable of achieving the same accuracy as the measured value obtained from the rotational speed detection means.

In addition, based on the rotary speed of the rotating shaft of the induction motor obtained in this manner, the present invention provides a rotary torque detection method of the rotating shaft of the induction motor and a device thereof.

In addition, based on the rotary torque of the rotating shaft of the induction motor obtained in this manner, the present invention provides a viscosity acquiring method of a material which is agitated by the induction motor and a method of manufacturing a material using the same.

Moreover, the present invention provides a rotary speed and a rotary torque detection method of a rotating shaft of an induction motor and a method for manufacturing a reaction product using a viscosity acquiring method of a material which is agitated by the induction motor.

Means for Solving the Problems

The inventors of the present invention focus on the slip of the induction motor. In other words, as is well known, slip S is specified by the rotary speed of the rotating magnetic field (synchronous speed) $N_S$ and the rotary speed of the rotor (actual rotary speed of the induction motor) N. In the induction motor, the slip S and the mechanical output PM are substantially proportional to each other up to the range of the rated mechanical output $P_0$ and rated slip $S_0$. Accordingly, by obtaining the slip S based on the relationship between the slip S and the mechanical output PM, the rotary speed of the rotating shaft of the induction motor can be obtained. Then, in the following, the unit of the rotary speed is treated as number of revolutions per minute $\text{min}^{-1}$.

However, the mechanical output PM is an unknown value. As shown in Patent reference 1, since the mechanical output PM is obtained by subtracting the loss power $P_L$ from the power input $P_I$, in order to obtain the loss power $P_L$ the rotary speed of the rotating shaft of the induction motor is necessary. Accordingly, the rotary speed of the rotating shaft of the induction motor cannot obtained simply based on the relationship between the slip S and the mechanical output PM.

Accordingly, the inventors of the present invention focus on dividing the loss power $P_L$ into the loss power A which does not depend on the rotary speed of the rotating shaft of the induction motor (hereinafter, represented as "non-depending loss power A") and the loss power B which depends on the rotary speed of the rotating shaft of the induction motor (hereinafter, represented as "depending loss power B"). Then, the present invention is completed by applying the approximate value of the mechanical output PM, which is calculated that merely the non-depending loss power A, except for the depending loss power B, is regarded as the loss power $P_L$, to the relationship between the slip S and the mechanical output PM so as to obtain the rotary speed of the rotating shaft of the induction motor.

In other words, the present invention relates to the rotary speed detection method of the rotating shaft of the induction motor which includes a process of dividing the loss power $P_L$ into the non-depending loss power A and the depending loss power B, wherein $P_L$ is the loss power when the power input $P_I$ is supplied to the induction motor, and the following step I, step II and step III are included.

Step I: The difference [P−A] between the power input $P_I$ and the non-depending loss power A is considered as a first order approximation value $PM_1$ of the mechanical output of the induction motor. Then, a first order approximation value of the rotary speed of the rotating shaft $N_1$ is obtained by setting $N_1 = N_S(1-S_1)$ from the correlated equation $PM_1 = \alpha S_1$ ($\alpha$ is the motor constant) of the given slip S of the induction motor and the mechanical output PM. In addition, $N_S$ is the motor constant called synchronous speed.

Step II: Based on the first order approximation value $N_1$, the depending loss power $B_1$ is obtained.

Step III: For the induction motor, a second order approximation value of the rotary speed, $N_2 = N_S(1-S_2)$ ($N_S$ is the synchronous speed), is obtained from the correlated equation $PM_2 = \alpha S_2$ ($\alpha$ is the motor constant) of the known mechanical output PM and the slip S. The second order approximation value $N_2$ is treated as a detected rotary speed of the rotating shaft.

By the speed detection method including the above mentioned step I to step III, without employing a measuring instrument, the rotary speed of the rotating shaft of the induction motor can be obtained with high accuracy.

In the case that the calculation of high rotary speed with higher accuracy is required, the second order approximation value $N_2$ (second approximation speed) obtained from the step III is substituted for the first order approximation value $N_1$ (first approximation speed) of the step I, and the step II and the step III are sequentially repeated.

Namely, the present invention includes a step IV in which the loss power $B_n$ can be obtained based on the $n^{th}$ order approximation value $N_n$, and a step V in which the $(n+1)^{th}$ order approximation value of the rotary speed of the rotating shaft of the induction motor $N_{(n+1)} = N_S(1-S_{n+1})$ ($N_S$ is the synchronous speed), can be obtained from the correlated equation $PM_{(n+1)} = \alpha S_{(n+1)}$ ($\alpha$ is the motor constant) of the known output PM and the slip S of the induction motor, wherein the $(n+1)^{th}$ order approximation value of the output of the induction motor $PM_{(n+1)}$ is considered as $P-(A+B_n)$. Provided that n is an integer equal to or greater than 2. Then, after the second order approximation value $N_2$ is obtained in the step III, the step IV and the step V are repeated for a predetermined number of times. In this way, the more orders of the approximate speed are obtained, such as the third order approximate speed, fourth order approximate speed, ..., $n^{th}$ order approximate speed, the more precise the rotary speed (actual rotary speed) of the rotating shaft of the induction motor is. However, the orders of approximate speed are obtained according to requirements. For some purposes the second order approximate speed may sufficiently satisfy the actual rotary speed. As described in the following exemplary embodiments, for the viscosity detection in the manufacturing process of the reaction liquid (resin solution), it is confirmed that the second order approximate speed can fully reflects the actual rotary speed.

The present invention provides a detection device which performs the above mentioned rotary speed detection method of the rotating shaft of the induction motor (the rotary speed detection device of the rotating shaft of the induction motor).

The detection device includes an information obtaining unit for obtaining the measurement information including power, current, voltage and voltage frequency supplied to the induction motor, and a calculation processing unit for obtaining the rotary speed via calculation based on the measurement information. The calculation processing unit performs the processing defined in the above mentioned step I, step II and step III.

It goes without saying that the calculation processing unit of the detection device can perform the processing of obtaining the third order approximate speed, fourth order approximate speed, ..., $n^{th}$ order approximate speed. In addition, it is the same as the following described rotary torque detection method and detection device of the rotating shaft of the induction motor, viscosity detection method of reaction liquid and viscosity detection device of reaction liquid, and manufacturing method of reaction product.

In the present invention, the rotary torque T of the rotating shaft of the induction motor can be detected by using the rotary speed (the $n^{th}$ order approximation value $N_n$, provided that n is an integer equal to or greater than 2) of the rotating shaft of the induction motor obtained in such a manner as described above. It is summarized that when the power input P is supplied to the induction motor, the rotary torque of the rotating shaft of the induction motor is detected by using the equation $T = (P-(A+B_1))/(2\pi \times N_2/60)$ based on the loss power A, the loss power $B_1$ obtained from the step II, and the second order approximation value $N_2$ of the rotary speed obtained from the step III.

The rotary torque detection device, which performs the detection method of rotary torque T, can be the above mentioned calculation processing unit of the rotary speed detection device of the rotating shaft of the induction motor with an additional function of performing the processing by using the equation $T = (P-(A+B_1))/(2\pi \times N_2/60)$ based on the loss power A, the loss power $B_1$, and the second order approximation value $N_2$.

In addition, in the present invention, by using the rotary torque T of the rotating shaft of the induction motor obtained as above described, the viscosity of the reaction liquid can be detected. In the viscosity detection method of the reaction liquid and the viscosity detection device of the reaction liquid disclosed in the present invention, the to-be-detected viscosity is the viscosity η of the reaction liquid when the reaction liquid is agitated by the rotation of agitation blade connected to the rotating shaft of the induction motor which serves as the power source. Specifically, the method for obtaining the viscosity η of the reaction liquid is the detection method of the viscosity of the above mentioned reaction liquid when the reaction liquid is agitated by the rotation of the rotating shaft, which includes an agitation blade, of the induction motor serving as the power source, and the rotary torque T of the rotating shaft is obtained by using the equation $T=(P-(A+B_1))/(2\pi \times N_2/60)$ based on the loss power A, the loss power $B_1$ obtained from the step II recited in claim 1, and the second order approximation value of the rotary speed of the rotating shaft $N_2$ obtained from the step III recited in claim 1, wherein the viscosity r) is obtained from the rotary torque T by using the equation $\eta=\kappa T/N$ (unit Pa·S). Herein, κ is the constant determined according to the dimensions of the agitation blade and the reaction vessel used to agitate the reaction liquid.

The device which performs the viscosity detection method of reaction liquid can be the above mentioned calculation processing unit of the rotary torque detection device with an additional function of performing the processing by using the equation $\eta=\kappa T/N$ (unit Pa·S) based on the second order approximation value $N_2$ of the rotary speed and the rotary torque T.

Moreover, the present invention provides a manufacturing method of a reaction product, wherein at least one kind of compound is used as a raw material. The viscosity of the reaction product is changed with the reaction process of the raw material when the reaction product is manufactured. Specifically, the method is characterized by including the detection method of rotary speed of the rotating shaft of the induction motor (first process), the detection method of rotary torque of the rotating shaft of the induction motor (second process) and the viscosity acquiring method of reaction product (third process).

Effect of the Invention

According to the present invention, the rotary speed can be detected with high accuracy without employing the speed measurement instrument as an entity. In addition, since using of an explosion-proof measurement instrument is unnecessary for the method and device of the present invention, not only the manufacturing cost of detection method and detection device of viscosity of reaction liquid can be reduced, the delivery period can also be shortened. Furthermore, in the manufacturing method of reaction product of the present invention, the viscosity of reaction product can be observed in real time. Therefore, the unstableness in the endpoint of the reaction of the manufacturing lot can be reduced and the stabilization of the physical properties of the product is resulted.

DESCRIPTION OF THE EMBODIMENTS

In the following, the present invention is described in detail in accordance with the drawings.

[Regarding the Slip S and the Mechanical Output PM]

The slip S, as well known, is specified by the following Equation (1), wherein the synchronous speed is $N_S$ and the rotary speed of the rotor (the actual rotary speed of the rotating shaft of the induction motor) is N.

$$S=(N_S-N)/N_S \tag{1}$$

And, Equation (1) is rewritten as Equation (1') so as to solve N.

$$N=N_S(1-S) \tag{1'}$$

In other words, the rotary speed of the rotating shaft of the induction motor can be obtained if the slip S can be specified. Then, the slip S is used so that the rotary speed of the rotating shaft of the induction motor is obtained in the present invention. In addition, the slip S is the basic characteristic provided with the induction motor.

Figure 1:
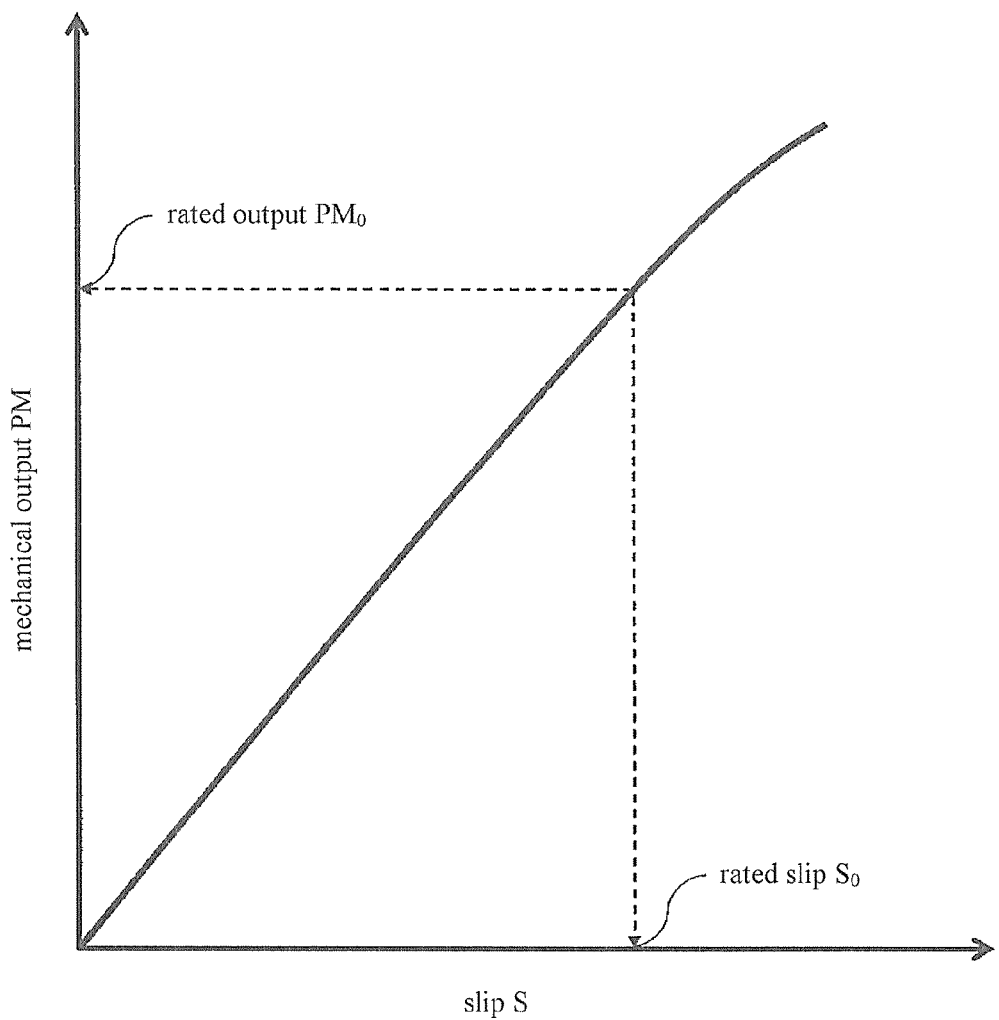
FIG. 1 is a graph showing the relationship between slip S and mechanical output PM of induction motor.

The relationship between the slip S and the mechanical output PM is shown in FIG. 1. Up to the range of rated mechanical output $PM_0$ and rated slip $S_0$, i.e., in the operation under the actual rated speed, the slip S and the mechanical output PM are substantially proportional to each other and in a linear correlation, and the correlation of the following Equation (2) is established.

In Equation (2), α is the specific constant of the induction motor, and the ratio of the rated mechanical output $PM_0$ to the rated slip $S_0$ is given as $PM_0/S_0$.

Consequently, if the mechanical output PM is known, the slip S can be obtained and the rotary speed (or the angular velocity) of the rotating shaft can be obtained.

$$PM=\alpha \times S \tag{2}$$

(α Represents the Motor Constant)

However, since the power input P supplied to the induction motor is consumed as an addition loss (loss power) of mechanical output PM by the induction motor, the following Equation (3) is concluded.

$$PM=P-P_L \tag{3}$$

Herein the loss power $P_L$ of the induction motor may consist of primary copper loss, second copper loss, iron loss, mechanical loss, floating loss and the like. And, each loss is generated by individual reasons in which the primary copper loss is the joule heat due to the electrical resistance of the stator winding wire and the secondary copper loss is the joule heat due to the electrical resistance of the rotor winding wire. In addition, the iron loss is the loss generated when any of rotation and magnetic field occurs and consists of hysteresis loss and eddy-current loss. Moreover, the mechanical loss is due to the friction or air drag generated by the rotation of the axis, and the floating loss is the constant of specific loss determined by the induction motor. The loss, except the floating loss, can be obtained by calculation using the voltage, the current, the power frequency, the rotary speed and the motor circuit constant during the operating of the induction motor (paragraphs [0028] to [0040] of Patent reference 1). The factor of each loss is described as follow.

[Factor of Loss $P_L$]
primary copper loss: $\propto$(first order current $I_1$)$^2$
eddy-current loss: $\propto$(first order voltage V)$^2$
hysteresis loss: $\propto$(first order voltage V)$^2$/(frequency f)
secondary copper loss: $\propto$(second order current $I_2$)$^2 \rightarrow \Phi(I_1, V, \omega)$
mechanical loss: $\propto$(angular velocity $\omega$)
floating loss: constant Each component of the loss power $P_L$ as mentioned above can be divided into the component which does not depend on the rotary speed (angular velocity $\omega$) (the non-depending loss power A)) and the component which depends on the rotary speed (the depending loss power B). Herein the non-depending loss power A can be specified by the current measurement instrument and voltage measurement included in Patent reference 1. Accordingly, Equation (3) can be rewritten into Equation (3').

$$PM=P-(A+B) \quad (3')$$

[non-depending loss power A] primary copper loss, eddy-current loss, hysteresis loss, floating loss

[depending loss power B] secondary copper loss, mechanical loss

Consequently, by excluding the depending loss power B (B=$B_0$=0), if only the non-depending loss power A is considered, the first order approximation value $PM_1$ of the mechanical output PM can be obtained from the following Equation (4).

$$PM_1=P-A \quad (4)$$

Thus, since the mechanical output (first order approximation value) is obtained, by using Equation (2), the first order approximation value of slip $S_1$ can be obtained from the following Equation (5).

$$S_1=PM_1/\alpha=PM_1 \times S_0/P_0 \quad (5)$$

Herein, $S_0$ is the rated slip and the $P_0$ is the rated mechanical output.

In addition, by applying Equation (1'), the first order approximation value of the rotary speed of the rotating shaft of the induction motor $N_1$ corresponding to the first order approximation value of slip $S_1$ can be obtained by using the following Equation (6). Herein, $N_S$ is the synchronous speed.

$$N_1=N_S(1-S_1) \quad (6)$$

The aforementioned is the description with respect to the rotary speed detection method of the rotating shaft of the induction motor of the present invention related to step I, and the method related to step II and step III is described as follows. In addition, the first order approximation value of the rotary speed $N_1$ obtained from step I can be treated as the detected result of the rotary speed according to the application purposes.

In step II, the first order approximation value $B_1$ of the depending loss power B corresponding to the first order approximation value of rotary speed of the rotating shaft of the induction motor $N_1$ obtained from step I is obtained by setting to k ($N_1$) according to the well-known correlation equation obtained by the analysis of equivalent circuit of induction motor. The details thereof are illustrated in [depending loss power $B_n$(W)].

In the proceeding step III, the second order approximation value of the mechanical output $PM_2$ obtained by substituting the non-depending loss power A and the first order approximation value of the depending loss power $B_1$ into Equation (3) can be obtained by the following Equation (7). In addition, the same as the processing of the first order approximation, through Equation (8) and Equation (9), the second order approximation value of rotary speed of the rotating shaft of the induction motor $N_2$ can be obtained. Since the component of depending loss power which is the first order approximation value $B_1$ is considered, the second order approximation value $N_2$ has a higher accuracy than the first order approximation value $N_1$ with respect to the actual rotary speed.

$$PM_2=P-(A+B_1) \quad (7)$$

$$S_2=PM_2/\alpha=PM_2 \times S_0/P_0 \quad (8)$$

$$N_2=N_S(1-S_2) \quad (9)$$

As described above, the rotary speed of the first order approximation of the rotating shaft of the induction motor is obtained in step I. The loss power depending on the rotary speed corresponding to the resulting speed is obtained in step II. The rotary speed of the second order approximation is obtained by incorporating the resulting loss component into the entire loss power in step III.

In order to obtain the rotary speed of a third order approximation from the rotary speed of the second order approximation, returning to the step II, the rotary speed of the first order approximation $N_1$ is replaced by the rotary speed of the second order approximation $N_2$, and the depending loss power $B_2$ corresponding to the speed at that time is obtained. By incorporating the loss power $B_2$ obtained in step II into the entire loss power in step III, the corresponding rotary speed can be obtained.

The proceeding from the third order to the fourth order can be performed by repeating step II and step III sequentially.

In the present invention, the more the number is repeated the closer the value of loss power $P_L$ approaching to the actual value is. Therefore, the rotary speed of the rotating shaft of the induction motor obtained by such a manner may become closer to the accurate value. However, in the present invention, the increasing of repeating number is not required. As shown in the following embodiments, the detection purpose of the rotary speed of the rotating shaft of the induction motor can be sufficiently achieved by using the second order approximate speed.

In addition, the mechanical output of $n^{th}$ order approximation, the rotary speed of the rotating shaft of the induction motor of $n^{th}$ order approximation and the depending loss power of $n^{th}$ order approximation are generally shown in the following.

$PM_n=P-(A+B_{(n+1)})$ the mechanical output of $n^{th}$ order approximation $N_n=N_S(1-S_n)$ the rotary speed of the rotating shaft of the induction motor of $n^{th}$ order approximation $B_n=\Phi(N_n)$ the depending loss power of $n^{th}$ order approximation Additionally, n of the above equations is an integer equal to or greater than 1, and $B_0$ is considered as zero.

[Viscosity Measurement]

Hereinafter the rotary speed detection method of the rotating shaft of the induction motor of the embodiment being applied to the measuring method and device of the viscosity of reaction liquid is described. In addition, in the process of viscosity detection, the rotary torque T of the rotating shaft of the induction motor is detected.

In the viscosity measurement of the present embodiment, the rotary torque T of the rotating shaft of the induction motor is obtained by using the following Equation (10) based on the power input P, the loss power $P_L$, the angular velocity $\omega$. Furthermore, the viscosity $\eta$ is obtained by the following Equation (11) based on the rotary torque T.

Though the rotary torque T and viscosity r are also obtained by using Equation (10) and Equation (11) in Patent reference 1, the point of the present embodiment that the loss power $P_L$ of Equation (10) and the angular velocity $\omega$ are based on the rotary speed obtained by the above mentioned detection method of the rotary speed of the rotating shaft of the induction motor is different from Patent reference 1. The details are described as follows.

$$T=(P-P_L)/\omega \tag{10}$$

$$\eta=\kappa T/N \text{ (unit Pa·S)} \tag{11}$$

Herein K is a constant determined according to the dimensions of the reaction vessel and the agitation blade used during the agitation of the reaction liquid is performed.

[Power Input P (W)]

In the present embodiment, the power input P is necessary so as to obtain the rotary torque T of the rotating shaft of the induction motor.

The power input measurement value is used as the power input P. A general power meter can be used in the measurement. It is necessary to properly use the power meter according to the type of the induction motor used. For instance, a single-phase power meter is used in the case that the induction motor is a single phase circuit, and a three-phase power meter is used for the three-phase induction motor.

[Loss Power $P_L$ (W)]

In addition, the loss power $P_L$ is necessary so as to obtain the rotary torque T of the rotating shaft of the induction motor.

As mentioned above, the loss power $P_L$ consists of the primary copper loss [$\propto$(first order current $I_1$)$^2$], the eddy-current loss [$\propto$(first order voltage V)$^2$], the hysteresis loss [$\propto$(first order voltage V)$^2$/(frequency f)], the secondary copper loss [$\propto\Phi(I_1, V, \omega)$], the mechanical loss [$\propto$(angular velocity $\omega$)] and the floating loss (constant).

[Non-Depending Loss Power A (W)]

Herein the primary copper loss, the eddy-current loss and the hysteresis loss can be calculated by using the measurement values obtained by the current measurement instrument for measuring current, the voltage measurement instrument for measuring the voltage and the frequency measurement instrument for measuring inverter output frequency. More specifically, the values can be obtained by using the voltage value, the current value, the frequency and the specific circuit constant of the induction motor during the rotation, and by performing a predetermined calculation. Herein the circuit constant can be obtained according to the testing table provided by the motor maker or the measurement values according to the loading test of the induction motor. In addition, the floating loss is provided as the specific value of the induction motor (specific loss (unit W)).

The primary copper loss, the eddy-current loss and the hysteresis loss can be generally described as follows.

primary copper loss=primary winding wire resistance×(one-phase current)$^2$×phase equation of induction motor eddy-current loss=eddy-current loss when rotating with rated voltage×(one-phase current measurement value/rated phase current)$^2$ (unit W)

hysteresis loss=hysteresis loss when rotating with rated voltage and rated frequency×(one-phase current measurement value/rated phase current)$^2$/(inverter output frequency measurement value/rated frequency) (unit Hz)

[Depending Loss Power $B_n$ (W)]

Regarding this, the secondary copper loss and the mechanical loss are component depending on the rotary speed of the rotating shaft of the induction motor and can be obtained by using the above mentioned depending loss power $B_n$. However, since the depending loss power $B_n$ cannot be obtained in the stage of obtaining the rotary speed of the first order approximation $N_1$ of the rotating shaft of the induction motor, only the non-depending loss power A is included in the loss power $P_L$, and in addition to the non-depending loss power A, the loss power $P_L$ may further include the depending loss power $B_1, B_2, \ldots$ and so on, after becoming the second order approximation.

For the secondary copper loss and the mechanical loss which are the depending loss power $B_n$, in addition to the above, the rotary speed of the $n^{th}$ order approximation $N_n$ of the rotating shaft of the induction motor can be obtained. In other words, if the angular velocity $\omega$ is set to be variable, since the correlation between the angular velocity $\omega$ and the rotary speed N is $\omega=2\pi N$ [rad/s], by substituting the rotary speed of the $n^{th}$ order approximation $N_n$ into each of the correlated equations of the secondary copper loss and the mechanical loss, the secondary copper loss and the mechanical loss can be obtained.

[Mechanical Output PM (W), Rotary Torque T (N·m)]

The mechanical output PM is the value obtained by subtracting various loss powers from the power input P. In the present embodiment, as described above, the mechanical output is obtained from the equation: $PM_n=P-(A+B_{(n-1)})$.

Then, the rotary torque T of the rotating shaft of the induction motor is obtained according to the above mentioned Equation (10) by using the rotary speed of the $n^{th}$ order approximation $N_n$, and the viscosity $\eta$ of liquid material can be obtained according to the above mentioned Equation (11) by using the obtained rotary torque T and the rotary speed of the $n^{th}$ order approximation $N_n$.

$$T_n=(P-P_L)/\omega=PM_n/\omega_n=PM_n/(2\pi \times N_n/60) \tag{10}$$

$$\eta_n=\kappa T_n/N_n \text{ (unit Pa·S)} \tag{11}$$

($\kappa$ is a constant determined according to the dimensions of the reaction vessel and the agitation blade used during the agitation of reaction liquid is performed.)

In the following, Equation (11) is described.

According to the Newton's equation, the force F generated when the two planes with area A sandwiching the liquid with thickness h moves in a relative speed U, and $\eta$ which represents the viscosity can be represented as the following Equation (12).

$$F=\eta AU/h \text{ (unit N)} \tag{12}$$

Figure 2:
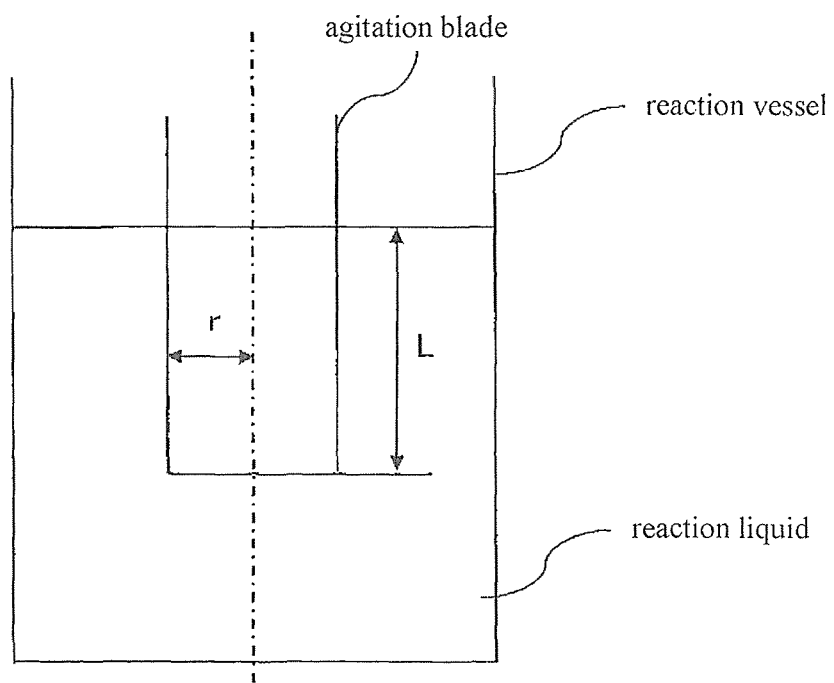
FIG. 2 is a schematic cross-section view of the dimensions of the vessel in which an agitation blade is disposed.

Herein in the reaction vessel shown in FIG. 2, r is radius of the agitation blade, L is the depth of the agitation blade submerged in the liquid material that is to be agitated, N is the number of revolutions, F is the force generated to the agitation blade when the agitation blade is agitated at a distance r, g is the distance between the agitation blade and the reaction vessel, and Equation (12) may become the following Equation (13).

$$F=\eta(2\pi rL \cdot 2\pi rN)/g \qquad (13)$$

Then, rotary torque $(T)=F \cdot r=\eta(2\pi rL \cdot 2\pi rN)/g \cdot r$ (unit $N \cdot m$)

and becomes $$\pi = T \cdot g/(2\pi rL \cdot 2\pi rN \cdot r)$$

However, the values, except T and N are determined according to dimensions of the reaction vessel and the agitation blade, may be changed. If the viscosity η is described as Equation (11), according to the present embodiment, the viscosity of liquid material can be relatively obtained.

$$\eta = \kappa T/N \qquad (11)$$

In the present embodiment, the output frequency can be obtained synchronously with the other measurement values such as power, voltage and current, and may be incorporated into various variables to determine loss. In the present embodiment, by incorporating the frequency measurement value for detecting the inverter output frequency into the hysteresis loss detection, the detected change (variation) of reaction liquid viscosity can be reduced, which is preferable for reaction process management.

[Synchronous Measurement]

In the present embodiment, in the case of time variation of a load being fast, the shift of measurement timing of each of the measurement instruments may break the assumption of law of conservation of energy in which the sum of energy input/output is zero. Therefore, it is preferable that the measurements of all the measurement instruments are performed synchronously. However, in the case when the time variation of load is gradual and the measurement values do not change substantially until the entire measurement values are obtained, limiting to a synchronous measurement is not needed.

Furthermore, in the case that the time variation of a load is dramatic, except for disposing the measurement instrument, a synchronous signal generating unit for outputting a measurement command synchronously with respect to each of the measurement instruments can be disposed so that measurement can be synchronously performed to each of the measurement instruments.

The specific applications applied to the rotary torque and rotary speed detection method of the rotating shaft of the induction motor of the above mentioned embodiments are not limited. An exemplary embodiment of the viscosity detection of reaction liquid is described. In the case of manufacturing a reaction liquid in which the viscosity varies according to the reaction process, by detecting the viscosity, the reaction process is manageable. In this case, the device is for detecting the rotary torque and the rotary speed of the shaft in which an induction motor is used as a power source, and for further detecting the viscosity of reaction liquid. The device includes a power measurement instrument for measuring the power, a current measurement instrument for measuring the current and a voltage measurement instrument for measuring the voltage supplied to the induction motor, and a frequency measurement instrument for measuring the inverter output frequency. Then, the device further includes a calculation processing unit for obtaining the viscosity of reaction liquid by calculation and obtaining the rotary speed and rotary torque of the rotating shaft of the induction motor by performing a predetermined calculation based on the measurement information obtained by each instrument. The measurement instruments of power, voltage, current and frequency can be known and commonly used instruments.

The reaction liquid mentioned in the present invention is a liquid whose viscosity varies with the reaction process in which at least one kind of compound is used as a raw material. In the present invention, the reaction liquid is the reaction product.

The elements which are commonly used and having processing functions such as various personal computers like notebook, desktop or the like, and process computer can be used in above mentioned calculation processing unit. In the calculation processing unit and each of the measurement instruments, the commonly used data communication functions such as RS-232C, GP-IP, USB, ISA, PCI, and the like can be included. In addition, the synchronous signal generating unit can used the command of computer.

In the following, a detection device 1 which performs the rotary speed and rotary torque detection method of the rotating shaft of the induction motor and the viscosity detection method of reaction liquid according to the present embodiment is described as an example with accompanying of FIG. 3.

The detection device 1 detects the rotary speed of the agitation blade 13 rotationally driven by the induction motor 9 when the reaction liquid supplied into the reaction vessel 12 is agitated in the reaction vessel. Herein, the reaction liquid can be a chemical reaction product.

The detection device 1 includes a measurement unit 2 and a calculation processing unit 5.

For example, a power meter of three-phase alternating circuit, a 4-channel voltage meter, a 4-channel current meter and a frequency meter are incorporated into one unit and packaged to form the measurement unit 2, wherein the measurement unit 2 is connected to the three-phase alternating circuit through voltage lead-in wires 6 and current lead-in wires 7. Additionally, the measurement unit 2 can also be formed by each of the measurement instruments being individually disposed.

Figure 3:
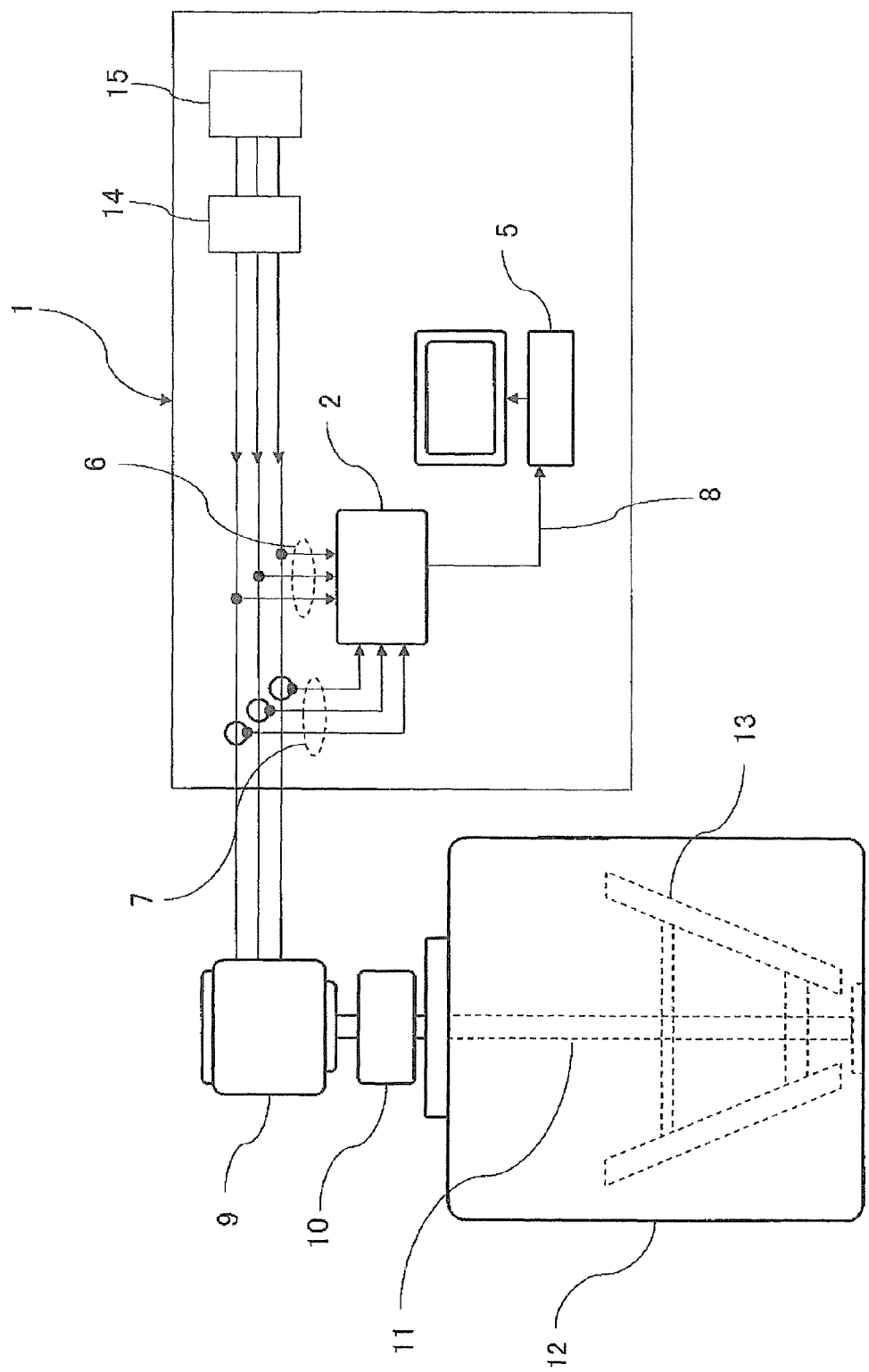
FIG. 3 is a schematic view of an agitation device of reaction liquid according to an exemplary embodiment.

Moreover, as shown in FIG. 3, the induction motor 9 which is the power source of the agitation blade 13 is assumed to be a three-phase circuit, and a commonly used power meter of three-phase can be used. In addition, in this case, the voltage and current are measured in each phase; thus, the rotary speed and rotary torque of the induction motor can be calculated at each phase and then combined. In addition, the present invention can also be applied to the case that the induction motor is a single-layer circuit or the direct current (DC) motor is driven by a DC power.

The calculation processing unit 5 includes a personal computer, for example. Herein, the power, the voltage, the current and the frequency are first measured in the measurement unit 2 by the control of the action of the measurement unit 2, and then the calculation processing is performed for obtaining the rotary speed and rotary torque of the rotating shaft of the induction motor. Then, the calculation processing unit 5 performs the calculation processing for obtaining the viscosity of the reaction liquid based on the results.

In the measurement unit 2, the measurement of each of the measurement instruments are performed synchronously with the command from the calculation processing unit 5 through the communication cables 8. The calculation processing unit maintains the program for executing the calculation processing to obtain the rotary speed and rotary torque of the rotating shaft of the induction motor and the viscosity of reaction liquid, and the information required for calculation processing of the specific loss of the induction motor 9. The calculation processing unit 5 performs the calculation processing for the rotary speed of the rotating shaft of the induction motor based on the measurement information, and outputs the results through the screen or the internal information recording unit.

The induction motor 9 is connected with the agitation shaft 11 through the speed reducer 10, wherein agitation blades 13 are mounted on the agitation shaft 11. The agitation blades 13 are disposed in the reaction vessel 12 and agitates the reactant supplied into the reaction vessel 12 along with the rotation of the rotating shaft of the induction motor 9. The induction motor 9 is provided with a power through the inverter 14 by the three-phase power source 15.

By the detection device 1 having such configuration mentioned above, the operator can observe the values of rotary speed and rotary torque of the rotating shaft of the induction motor and viscosity of reaction liquid displayed on the monitoring screen of the calculation processing unit 5 in real time.

In addition, in the present invention, since the high linear relationship between the motor output and the slip is used for performing the rotary speed detection of the rotating shaft of the induction motor, error is increased in the high output region where the linearity is destroyed (beyond the rated output). However, in the industry, especially in the process of resin manufacturing with a chemical reaction, the application of the induction motor is mostly under the rated output and around 50% of the rated output; thus, there is no error problem.

[Temperature Compensation of Winding Coil Resistance]

By the way, the winding wire resistance is used to obtain the primary copper loss and the value of winding wire resistance is provided at the reference temperature (20° C.). Therefore, when the primary copper loss is calculated, by compensating the temperature to the actual operating temperature, the detection accuracy of the rotary speed and rotary torque of the rotating shaft of the induction motor and the viscosity of the reaction liquid can be improved. The following equation is used in compensating the resistance value at the operating temperature.

winding wire resistance at operating temperature=winding wire resistance at reference temperature×(operating temperature+234.5)/(20+234.5) (unit Ω)

Herein, the value 234.5 is known as the temperature coefficient of resistance of copper. Since it is difficult to directly measure the winding wire temperature during rotation, the temperature detection unit is fixed and disposed at a location which represents the entire temperature of the internal of the motor, and the resulting value can be considered approximately as the primary and secondary winding wire temperature.

[Null Torque Compensation]

The torque obtained according to Equation (10) includes the torque generated by the mechanical friction of reducer and bearings even when there is nothing in the reaction vessel (hereinafter it is called a null torque). Herein, if the null torque under the adopted agitating speed during the manufacturing of the reaction product is detected in advance and set to be a constant value, and the constant value is subtracted from the detected torque value when the viscosity is obtained by Equation (11), then the detection accuracy of viscosity can be improved.

[temperature compensation of viscosity]

Generally speaking, since the reaction temperature is determined by each product, the reaction vessel has a temperature control function. Though compensation is unnecessary when the effect of viscosity of temperature control error can be neglected, actually the error of ±1 to ±3° C. is inevitable. Therefore, in the present invention, in order to obtain the specific viscosity value of the reaction liquid at the predetermined temperature, by disposing a temperature detection device for detecting the reaction liquid temperature inside the reaction vessel and a temperature compensation unit for compensating the viscosity value of the reaction liquid based on the temperature value obtained by the temperature detection device, the compensated value of viscosity at the particular predetermined temperature can be output.

The temperature compensation of viscosity of reaction product is described in detail as follows. In the process of temperature compensation of viscosity of reaction product, in advance, the relationship between the viscosity and the temperature of the reaction product (temperature characteristic) is clearly understood. For instance, the temperature characteristic is described as a graph shown in FIG. 4. In the graph, $T_0$ represents the standard temperature when the reaction liquid is manufactured. The vertical axis represents the relative values at different temperatures of the value at temperature $T_0$ of viscosity which is obtained by the method of the present invention and set to be 100 (hereinafter viscosity %). By using the viscosity measurement instrument such as Gardner Holdt method to measure the temperature characteristic of the viscosity of reaction liquid in advance, and then based on the result, the curve can be created.

Figure 4:
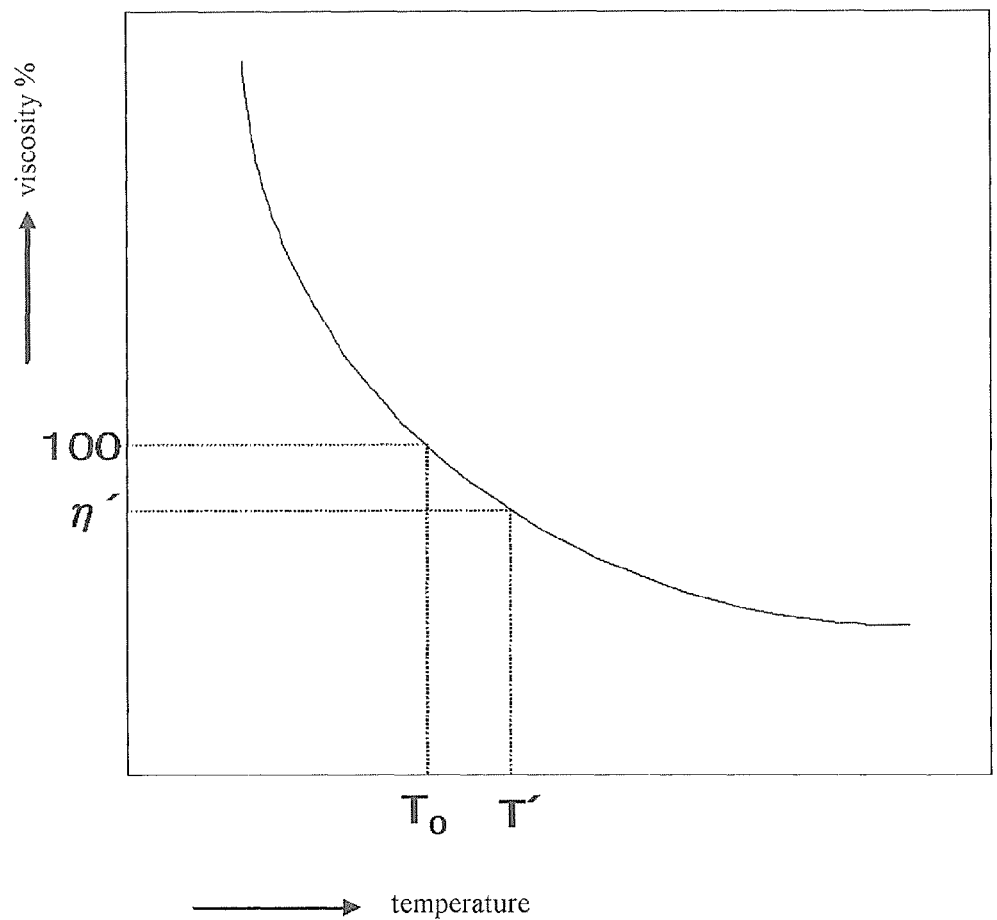
FIG. 4 schematically shows the temperature characteristics of viscosity of a typical reaction liquid.

Compensating the viscosity of the reaction product is performed as follows. The temperature curve shown in FIG. 4 is stored in advance in the memory of a PC of the aforementioned calculation processing unit 5 in a second or third order polynomial form. Then, the viscosity at the standard temperature 100 is divided by the value of viscosity % obtained by the temperature measurement instrument, and the result (hereinafter temperature compensation coefficient) is multiplied by the value obtained by Equation (11). Accordingly, the type of polynomial is not limited as long as the error of the relationship between the viscosity and the temperature represents the minimum.

On the contrary, if the liquid temperature inside the reaction vessel during the manufacturing of the reaction product is at the standard temperature $T_0$, since the viscosity value % is 100, the temperature compensation coefficient becomes 1; thus, the value may not change when it is multiplied by the value obtained by Equation (11). Similarly, in the case that the liquid temperature T' is higher than the standard temperature $T_0$, since the value of viscosity % η' becomes smaller than the value 100 obtained according to the temperature—viscosity % curve, the temperature compensation coefficient becomes greater than 1. By multiplying the result to the value obtained by Equation (11), the viscosity value detected at the actual temperature T' can be output in terms of the value of standard temperature $T_0$.

[Supply Amount Compensation of Viscosity]

In addition, in the present embodiment, when the standard supply amount of production per unit of the reaction vessel which is predetermined and the actual supply amount of production per unit are different, the supply amount compensation can be performed by compensating the viscosity value of the reaction liquid based on the difference between those two supply amounts. Herein, the supply amount refers to the supply mass or the supply volume, but generally the supply amount refers to the supply mass.

The manufacturing of reaction product is to supply the raw materials into the reaction vessel 12 according to requirements of customers and production schedule and so on, but the production amount of the production per unit is not constant. In the case that the total amount of raw materials supplied into the reaction vessel is increased or decreased, the rotary torque of the rotating shaft of the induction motor obtained by Equation (10) may be increased or decreased. Accordingly, the viscosity of reaction product obtained according to Equation (11) may be increased or decreased; thus, the value of specific viscosity of reaction liquid cannot be uniquely determined.

The supply amount compensation is performed as follows. In advance, the relationship between the supply amount of the reaction product and the viscosity is clearly understood. The relationship is described as the graph shown in FIG. 5. For example, the graph can be obtained by actually measuring the viscosity by varying the supply amount, and can also be obtained by using a CAE (computer aided engineering) simulation.

Figure 5:
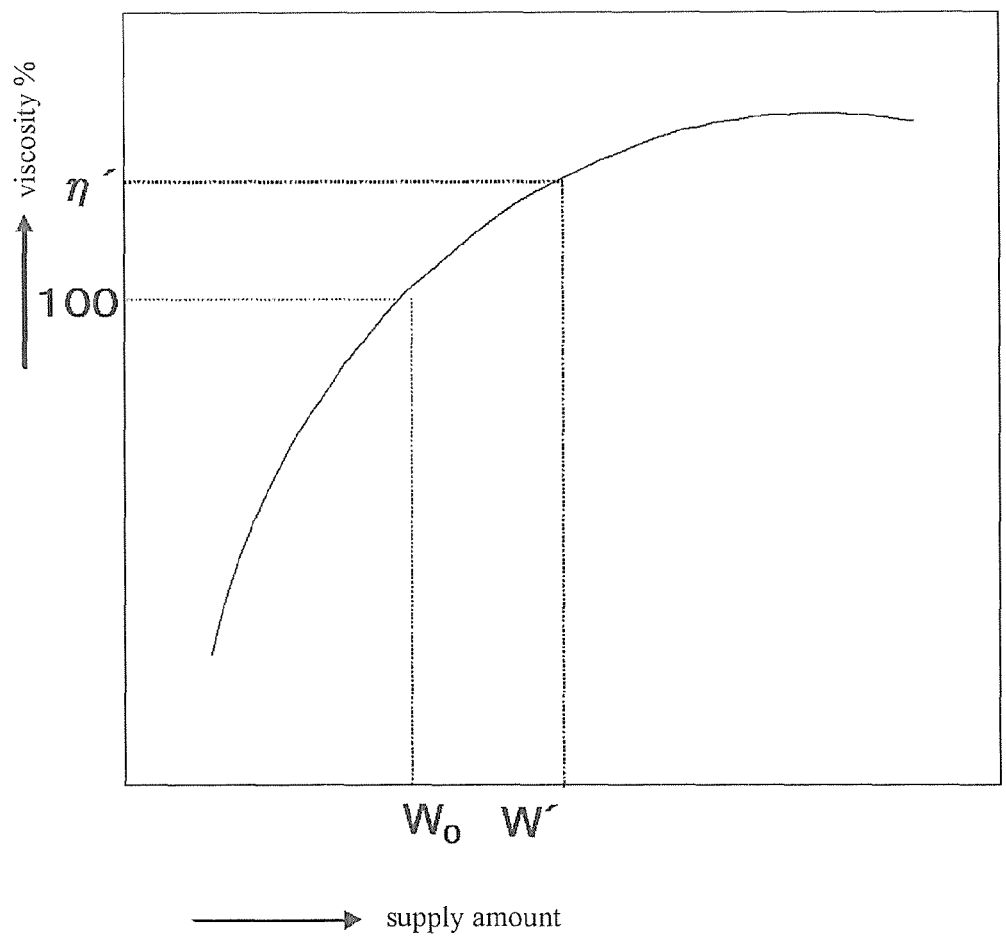
FIG. 5 shows that the values of viscosity of reaction liquid detected by changing the supply amount of raw material to the reaction vessel 9 are schematically shown in a curve.

In FIG. 5, the vertical axis represents the relative values of the viscosity obtained according to the method of present invention at other supply amounts which are different than the standard supply amount $W_0$ at which the value is 100 (hereinafter viscosity %). In the present invention, the supply amount compensation is performed as follows. The curve shown in FIG. 5 is stored in advance in the memory of PC of the aforementioned calculation processing unit 5 in a second or third order polynomial form. Then, the value 100 is divided by the value of viscosity % of the supply amount at the production process, and the result (hereinafter supply amount compensation coefficient) is multiplied by the value obtained by Equation (11). Accordingly, the type of polynomial is not limited as long as the error of the relationship between the viscosity and the supply amount represents the minimum.

On the contrary, if the supply amount supplied into the reaction vessel is the standard supply amount $W_0$, since the viscosity value is 100, the supply amount compensation coefficient becomes 1, and thus the value may not change when it is multiplied by the value obtained by Equation (11). Similarly, in the case that the supply amount W' is greater than the standard supply amount $W_0$, since the value of viscosity % if becomes greater than the value 100 obtained according to the curve of FIG. 5, the supply amount compensation coefficient becomes smaller than 1. By multiplying the result to the value obtained by Equation (11), the viscosity value detected at the actual supply amount W' can be output in terms of the value of standard supply amount $W_0$.

Moreover, the endpoint of reaction determining unit determines the detected viscosity of the reaction liquid calculated according to the above mentioned unit is the endpoint of the reaction when the detected viscosity exceeds a predetermined value.

By using the rotary speed detection method of the rotating shaft of the induction motor, the rotary torque detection method of the rotating shaft of the induction motor and the viscosity detection method of reaction liquid of the present invention in the reaction process of the raw material when a reaction product is manufactured in which at least one kind of compound is used as a raw material, the reaction product whose viscosity varies with the reaction process can be manufactured. The manufacturing method for manufacturing the reaction product specifically includes the following processes.

In the manufacturing method of a reaction product wherein at least one kind of compound is used as raw material of the reaction product, in the reaction process of the raw material, the viscosity of the reaction product varies with the reaction process.

The reaction is performed inside a reaction vessel which performs the agitation of the reaction product by the rotation of the rotating shaft of an induction motor which is used as a power source and having agitation blades.

During the reaction, the processes described as follows are included:

Step I: the loss power when the power input P of the induction motor is supplied is set to be $P_L$, and the loss power $P_L$ is divided into a non-depending loss power A which does not depend on the rotary speed of the rotating shaft of the induction motor and a depending loss power B which depends on the rotary speed.

The difference between the power input P and the loss power A is considered as the first order approximation value of the mechanical output of the induction motor $PM_1$, the first order approximation value of the rotary speed of the rotating shaft $N_1=N_s(1-S_1)$ ($N_s$ is the synchronous speed) is obtained from the correlation equation $PM_1=\alpha S_1$ ($\alpha$ is the motor constant) between the given output PM of the induction motor and the slip S.

Step II: The loss power $B_1$ is obtained based on the first order approximation value $N_1$.

Step III: The second order approximation value of output of the induction motor $PM_2$ is considered as $P-(A+B_1)$, the second order approximation value of the rotary speed of the rotating shaft $N_2=N_s(1-S_2)$ ($N_s$ is the synchronous speed) is obtained from the correlation equation $PM_2=\alpha S_2$ ($\alpha$ is the motor constant) between the given output of the induction motor PM and the slip S.

The first process is for detecting the rotary speed by using the rotary speed detection method of the rotating shaft of the induction motor including step I, step II and step III.

The second process is for detecting the rotary torque by using the detection method of the rotary torque. Based on the loss power A, the loss power $B_1$ obtained from the step II, and the second order approximation value of the rotary speed $N_2$ obtained from the step III, by using the following equation $$T=(P-(A+B_1))/(2\pi \times N_2/60)$$

the rotary torque of the rotating shaft of the induction motor is detected.

The third process is for obtaining the viscosity $\pi$ of the reaction product by using the following equation from the rotary torque T obtained from the detection process of the rotary torque.

$\eta \kappa T/N$ (unit Pa·S, $\kappa$ is the constant determined according to the dimensions of the agitation blade and the reaction vessel used to agitate the reaction liquid.)

In the above mentioned manufacturing method of the reaction product of the present invention, there is no particular limitation to the compound served as raw material, as long as the viscosity of the reaction product varies with the reaction process of the compound. According to the manufacturing method of the present invention, a reaction product whose viscosity is increased, such as resin, can be manufactured by polymerization and condensation of raw material with the reaction process, and a reaction product whose viscosity is reduced can also be manufactured by sealing the functional groups of the resin, such as the carboxyl group and the hydroxyl group, by using the compound having group which reacts with those functional groups (e.g., epoxy resin, carboxyl group, and the like).

The reaction product, for example, includes synthetic resin, polymerizable monomer, and the like. The polymerized resin, for example, includes polyethylene, polypropylene, polyvinyl chloride, polyvinylidene chloride resin, ABS (acrylonitrile butadiene-styrene resin) resin, polystyrene, acrylic resin, polyvinyl alcohol, epoxy resin, polyester resin, phenol resin, and polyurethane resin.

When polyethylene as a reaction product is manufactured, ethylene as a raw material is used, and various reactions such as high-pressure process, medium-pressure process, low-pressure process and the like are performed inside the reaction vessel in which the agitation of the reaction product is performed by using the rotation of the rotating shaft having agitation blades of the induction motor which serves as the power source. During the reaction process, viscosity of the reaction product can also be obtained by using the aforementioned processes.

When polypropylene as a reaction product is manufactured, propylene as a raw material is used, and various reactions such as BASF process, air layer method and the like are performed inside the reaction vessel in which the agitation of the reaction product is performed by using the rotation of the rotating shaft having agitation blades of the induction motor which serves as the power source. During the reaction process, viscosity of the reaction product can also be obtained by using the aforementioned processes.

When polyvinyl chloride as a reaction product is manufactured, vinyl chloride monomer as a raw material is used, and various reactions such as acetylene process, ethylene·acetylene process, oxychlorination process and the like are performed inside the reaction vessel in which the agitation of the reaction product is performed by using the rotation of the rotating shaft having agitation blades of the induction motor which serves as the power source. During the reaction process, viscosity of the reaction product can also be obtained by using the aforementioned processes.

When polyvinylidene chloride as a reaction product is manufactured, vinylidene chloride monomer as a raw material is used, and various reactions such as ion and free radical polymerization process are performed inside the reaction vessel in which the agitation of the reaction product is performed by using the rotation of the rotating shaft having agitation blades of the induction motor which serves as the power source. During the reaction process, viscosity of the reaction product can also be obtained by using the aforementioned processes.

When ABS resin as a reaction product is manufactured, butadiene, styrene or acrylonitrile as a raw material is used, and various reactions such as emulsion polymerization process, bulk polymerization process, solution polymerization process and the like are performed inside the reaction vessel in which the agitation of the reaction product is performed by using the rotation of the rotating shaft having agitation blades of the induction motor which serves as the power source. During the reaction process, viscosity of the reaction product can also be obtained by using the aforementioned processes.

When polystyrene resin as a reaction product is manufactured, styrene as a raw material is used, and the reaction of suspension polymerization process of styrene is performed inside the reaction vessel in which the agitation of the reaction product is performed by using the rotation of the rotating shaft having agitation blades of the induction motor which serves as the power source. During the reaction process, viscosity of the reaction product can also be obtained by using the aforementioned processes.

When acrylic resin as a reaction product is manufactured, acrylic monomer as a raw material is used, and the reaction of suspension polymerization process is performed inside the reaction vessel in which the agitation of the reaction product is performed by using the rotation of the rotating shaft having agitation blades of the induction motor which serves as the power source. During the reaction process, viscosity of the reaction product can also be obtained by using the aforementioned processes.

The acrylic monomer, for example, includes (meth)acrylates such as methyl(meth)acrylate, ethyl(meth)acrylate, butyl(meth)acrylate, cyclohexyl(meth)acrylate, phenyl (meth)acrylate, benzyl(meth)acrylate, 2-ethylhexyl(meth) acrylate, 2-hydroxyethyl(meth)acrylate and the like, and polyfunctional(meth)acrylates such as ethylene glycol dimethacrylate, diethylene glycol dimethacrylate, neopentyl glycol dimethacrylate and the like. Herein, only one or a combination of two or more of those can be used. Herein, (meth)acrylates refer to acryl or methacryl.

In the polymerization of acrylic monomer, a common polymerization initiator can be used and includes, for example, azo polymerization initiators such as 2,2'-azobis(2,4-dimethyl-4-methoxy valeronitrile), 2,2'-azobis(2,4-dimethyl valeronitrile), 2,2'-azobisisobutyronitrile, 2,2'-azobis(2-methylbutyronitrile), 2,2'-azobis[2-(2-imidazolin-2-yl)propane], dimethyl-2,2'-azobis(2-methylpropionate) and the like, and peroxide-based polymerization initiator such as bis (4-tert-butylcyclohexyl) peroxydicarbonate, di(2-ethylhexyl) peroxydicarbonate, di-n-propyl peroxydicarbonate, diisopropyl peroxydicarbonate, 1,1,3,3-tetramethylbutyl peroxyneodecanoate, 1-cyclohexyl-1-methylethyl peroxyneodecanoate, tert-butyl peroxyneodecanoate, tert-hexyl peroxyneodecanoate, tert-hexyl peroxypivalate, tert-butyl peroxypivalate, 1,1,3,3-tetramethylbutyl peroxy-2-ethylhexanoate, tert-hexyl-peroxy-2-ethylhexanoate, tert-butyl-peroxy-2-ethylhexanoate, octanoyl peroxide, lauroyl peroxide, benzoyl peroxide, 4-methoxy benzoyl peroxide and the like.

When polyvinyl alcohol as a reaction product is manufactured, ethylene and vinyl acetate as a raw material is used, and radical polymerization is performed inside the reaction vessel in which the agitation of the reaction product is performed by using the rotation of the rotating shaft having agitation blades of the induction motor which serves as the power source. During the reaction process, viscosity of the reaction product can also be obtained by using the aforementioned processes.

When epoxy resin as a reaction product is manufactured, a compound having a phenolic hydroxyl group and epihalohydrin as raw materials are used, and copolymerization of the compound having a phenolic hydroxyl group and epihalohydrin is performed inside the reaction vessel in which the agitation of the reaction product is performed by using the rotation of the rotating shaft having agitation blades of the induction motor which serves as the power source.

During the reaction process, viscosity of the reaction product can also be obtained by using the aforementioned processes. The compound having a phenolic hydroxyl group includes compound having hydroxyl group in the molecule of the reactant, for example, divalent phenol such as hydroquinone, resorcinol, catechol, dinaphthol and the like, bisphenols such as bisphenol A, bisphenol F, bisphenol S, bisphenol AD tetrabromobisphenol A and the like, biphenols such as biphenol tetramethyl biphenol and the like, phenols such as phenol novolak, cresol novolak, bisphenol A novolak, bisphenol F novolak and the like, and novolak resin obtained from formaldehyde, naphthols such as mononaphthol novolak, dinaphthol novolak, bis(2,7-dihydroxy naphthyl)-1,1-methane, (2-hydroxy naphthyl)-1-(2,7-dihydroxy naphthyl)-1-methane, bis(2-hydroxy naphthyl)-1,1-methane and the like, naphthol novolak resin obtained from formaldehyde, polyfunctional naphthol, unsaturated alicyclic hydrocarbon such as phenol, cresol, bisphenol, naphthol dicyclopentadiene and the like.

The epihalohydrin includes epichlorohydrin, epibromohydrin, β-methyl epichlorohydrin and the like, for example.

When polyester resin as a reaction product is manufactured, polybasic acids and polyhydric alcohols as raw materials are used, and condensation of the above mentioned alcohols and acids is performed inside the reaction vessel in which the agitation of the reaction product is performed by using the rotation of the rotating shaft having agitation blades of the induction motor which serves as the power source. During the reaction process, viscosity of the reaction product can also be obtained by using the aforementioned processes.

The dicarboxylic acid in which polybasic acids are used includes aliphatic diprotic acid such as maleic acid, maleic acid anhydride, fumaric acid, itaconic acid, itaconic acid anhydride, oxalic acid, malonic acid, succinic acid, succinic acid anhydride, adipic acid, azelaic acid, sebacic acid, decane-1,10-dicarboxylic acid and the like, and aromatic or alicyclic diprotic acid such as phthalic acid, phthalic acid anhydride, tetrahydrophthalic acid and its anhydride, hexahydrophthalic acid and its anhydride, tetrabromophthalic acid and its anhydride, tetrachlorophthalic acid and its anhydride, chlorendic acid and its anhydride, himic acid and its anhydride, isophthalic acid, terephthalic acid, cyclohexane dicarboxylic acid, 2,6-naphthalene dicarboxylic acid and the like.

In addition, as for one of the polyprotic acid having three or more functional groups, carboxylic acid having three or more carboxyl groups in one molecule and reactive derivatives thereof can be used and typically trimellitic acid anhydride, methylcyclohexene trimellitic acid, methylcyclohexene trimellitic acid anhydride, pyromellitic acid, pyromellitic dianhydride and the like are included.

The polyhydric alcohols includes aliphatic diol such as polyalcohol, ethylene glycol, 1,2-propylene glycol, 1,4-butanediol, 1,5-pentanediol, 1,6-hexanediol, diethylene glycol, dipropylene glycol, triethylene glycol, neopentyl glycol and the like, bisphenol such as bisphenol A, bisphenol F and the like, hydrogenated bisphenol A such as ethylene oxide adduct of bisphenol A, propylene oxide adduct of bisphenol A, alkylene oxide adduct of bisphenol A, xylylene diglycol and cyclohexanedimethanol, alkylene glycol and alicyclic diol.

The polyhydric alcohols having three or more functional groups can use compounds having three or more hydroxyl groups typically including glycerine, trimethylolethane, trimethylolpropane, sorbitol, 1,2,3,6-hexanetetrole, 1,4-sorbitan, pentaerythritol, dipentaerythritol, 2-methyl propanetriol, 1,3,5-trihydroxybenzene, tris(2-hydroxyethyl)isocyanurate and the like.

When phenolic resin as a reaction product is manufactured, phenol and formaldehyde as raw materials are used, and polymerization of phenol and formaldehyde is performed inside the reaction vessel in which the agitation of the reaction product is performed by using the rotation of the rotating shaft having agitation blades of the induction motor which serves as the power source. During the reaction process, viscosity of the reaction product can also be obtained by using the aforementioned processes.

When polyurethane resin as a reaction product is manufactured, polyisocyanate and polyol as raw materials are used, and polymerization of polyisocyanate and polyol is performed inside the reaction vessel in which the agitation of the reaction product is performed by using the rotation of the rotating shaft having agitation blades of the induction motor which serves as the power source. During the reaction process, viscosity of the reaction product can also be obtained by using the aforementioned processes.

The polyisocyanates includes aromatic diisocyanate compound such as p-phenylene diisocyanate, m-phenylene diisocyanate, p-xylene diisocyanate, m-xylene diisocyanate, 2,4-tolylene diisocyanate, 2,6-tolylene diisocyanate, 4,4'-diphenylm ethane diisocyanate, 3,3'-dimethyldiphenyl-4,4'-diisocyanate, 3,3'-diethyldiphenyl-4,4'-diisocyanate, 1,3-bis(α,α-dimethyl isothiocyanatomethyl)benzene, tetramethyl xylene diisocyanate, diphenylene ether-4,4'-diisocyanate, naphthalene diisocyanate and the like, and aliphatic diisocyanate compound such as hexamethylene diisocyanate, lysine diisocyanate, triinethylhexamethylene diisocyanate, isophorone diisocyanate, 4,4'-dicyclohexylmethane diisocyanate, hydrogenated xylene diisocyanate, norbomane diisocyanate and the like.

The polyol includes propylene glycol, ethylene glycol, glycerine, pentaerythritol and the like, for example.

EXAMPLES

In the following, as an example, the manufacturing of a resin by an application of the present invention is described.

In addition, in the manufacturing of resin, the device shown in FIG. 3 is used. The specification of the induction motor is as follows.

Specification of a three-phase induction motor (Y connection)

Capacity: 37 kW
Rated speed: 1479 revolutions per min (rated slip 0.014)
Rated voltage: 220V
Rated current: 124 A
Rated frequency: 50 Hz
Number of poles: 4
Primary winding wire resistance: $0.0328\Omega$
Primary winding wire reactance: $0.0446\Omega$ (at the rated frequency)
Secondary winding wire resistance: $0.0130\Omega$
Secondary winding wire reactance: $0.0430\Omega$ (at the rated frequency)
Resistance measurement reference temperature: 20° C.
Resistance temperature coefficient: 234.5
Mechanical loss: 160 W (at the rated speed)
Iron loss: 465 W (hysteresis loss 230 W, eddy-current loss 235 W)
Floating loss: 382 W
Agitation blade speed reduction ratio: 29:1

Example 1

Fabrication of Urethane Resin

Diethylene glycol and toluene diisocyanate (2, 4 body:2, 6 body at mass ratio of equal to or more than 95:equal to or less than 5) are used as raw materials of the urethane resin.

Since the reaction of diethylene glycol and toluene diisocyanate is an exothermic reaction, if toluene diisocyanate, which is the raw material, is put in at one time, an explosive reaction would occur. Therefore, diethylene glycol is put into the reaction vessel 12 shown in FIG. 1 in advance, and then in consideration of safety, toluene diisocyanate is divided into small portions and put in little by little to fabricate urethane resin.

The standard supply amount of the reaction vessel 12 in the manufacturing process which is used in the present example is 5000 kg, and the supply amount of the present example is 4500 kg. The supply amount compensation coefficient obtained by the supply amount compensation curve is 1.09. In the example, the standard temperature during the reaction of the manufacturing process of the product is 80° C., and the reaction temperature in the example is 78° C. In addition, the temperature compensation coefficient at 78° C. obtained by the temperature compensation curve of the product is 0.97.

Clamp-on power meter CW240 (Yokogawa Meters & Instruments Corporation) is used as the measurement unit 2.

The measurement instrument combines the power meter, 4-channel voltage meter, 4-channel current meter and frequency meter of three-phase alternating circuit and incorporates the four functions into a unit. Other measurement instruments beside the CW240 can also be used as long as having the same measurement functions.

The calculation processing unit (PC) 5 obtains the data from the measurement unit 2 by the communication unit and has a calculation function for calculating the rotary speed and rotary torque of the rotating shaft of the induction motor by performing a predetermined calculation and a synchronous signal generating unit for generating a measurement timing signal synchronously corresponding to each of the measurement instruments. Each of the measurement instruments synchronously performs a predetermined number of times of measurement per unit time according to the command of the calculation processing unit 5, and then the calculation processing unit 5 captures the average value and the rotary speed and rotary torque are calculated.

Figure 6:
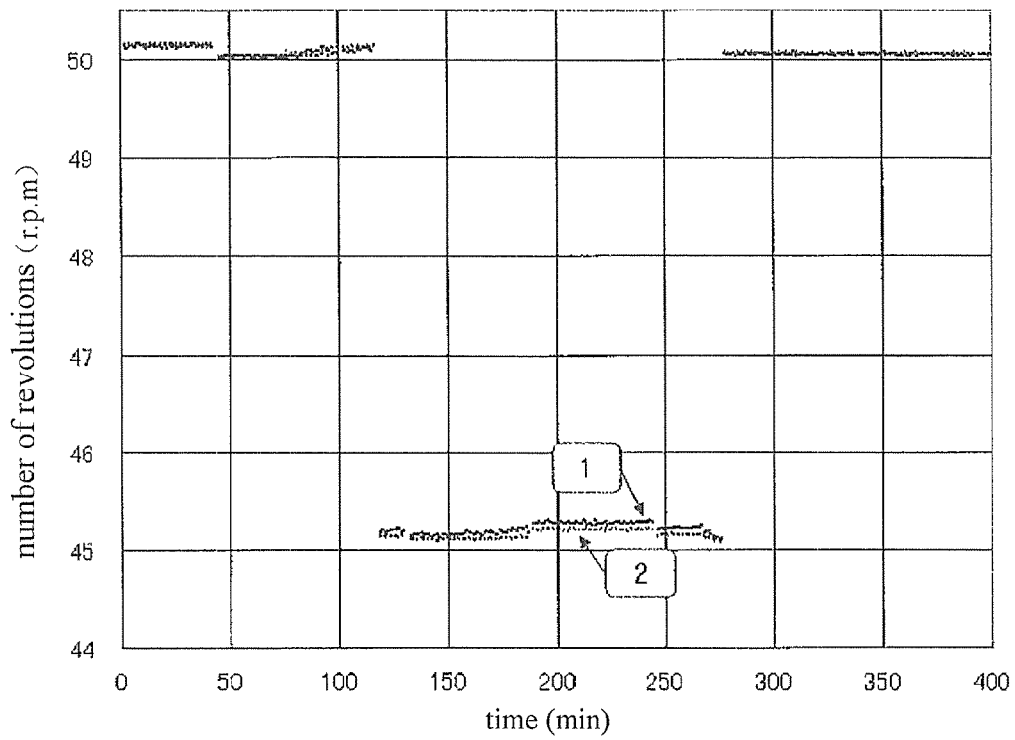
FIG. 6 shows a chart illustrating both the detected rotary speed (second approximation value $N_2$) of the rotating shaft of the induction motor by employing the present invention and the rotary speed of the actual rotary speed.
Figure 7:
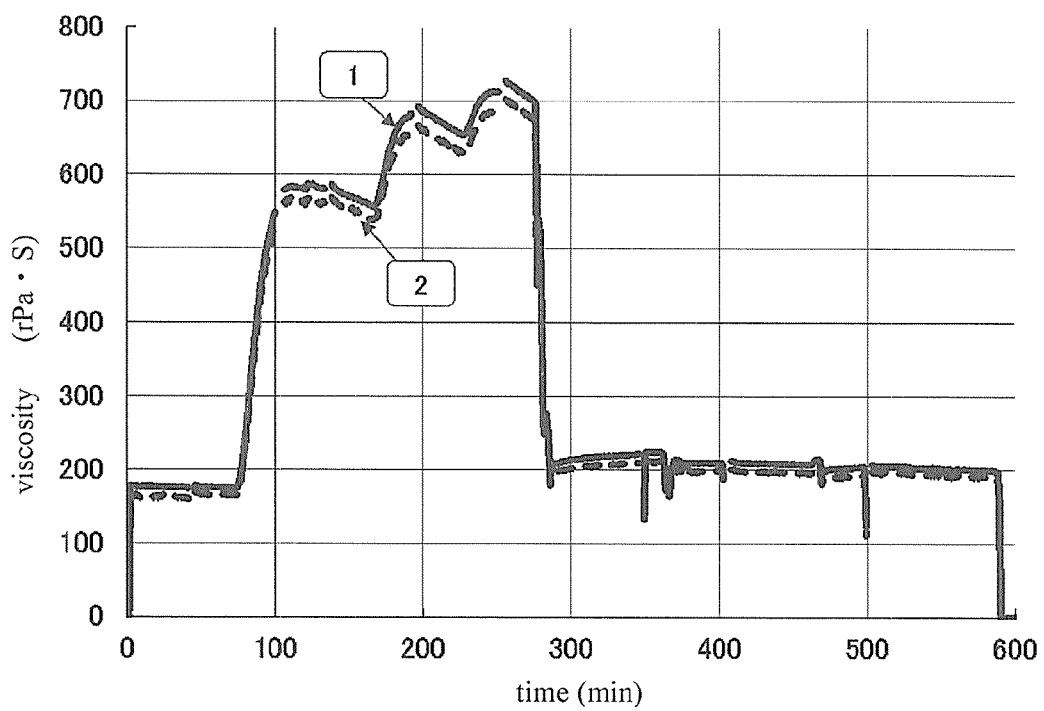
FIG. 7 shows a chart illustrating both the detected viscosity of reaction liquid by employing the present invention and the detected viscosity of reaction liquid by employing Patent reference 1.

FIG. 6 shows a chart illustrating both the detected rotary speed (second approximation value $N_2$ shown as "1" in the figure) of the rotating shaft of the induction motor by employing the present invention and the actual rotary speed (shown as "2" in the figure). In addition, FIG. 7 shows a chart illustrating both the detected viscosity (shown as "1" in the figure) of reaction product (urethane resin) by employing the present invention and the detected viscosity (shown as "2" in the figure) of the reaction product by employing Patent reference 1. Especially, even though in the case that the rotary speed changes rapidly, the detected rotary speed follows the actual rotary speed.

As shown in FIG. 6, the difference between the detected rotary speed of the rotating shaft of the induction motor of the present example and the actual rotary speed is small, and it is known that the actual rotary speed is affected. In addition, as shown in FIG. 7, although there is a slight difference between the detected viscosity of the example and the detected viscosity by the method of Patent reference 1, the detected viscosity of the example has a sufficient accuracy on the detection of the relative change of the viscosity in the reaction process. Therefore, the objective of detecting the viscosity of urethane resin can be fully achieved by using the detection of the relative change of viscosity. Moreover, the notations of viscosity units in FIG. 7 is added with a prefix r and conveniently expressed as rPa·S in order to differentiate from the output of the compensated conventional viscosity measurement instrument. The relative viscosity displayed as rPa·S numerically includes specific values of the agitation system consisting of the induction motor, the speed reducer and the agitation blades; thus, if the agitation system is changed, these values will also be entirely increased or decreased. However, there is no trouble on the detection of the relative change of the viscosity in the system.

(Discussion of the Correlativity Between the Viscosity Value Obtained by the Method of Present Invention and the Control Value)

Figure 8:
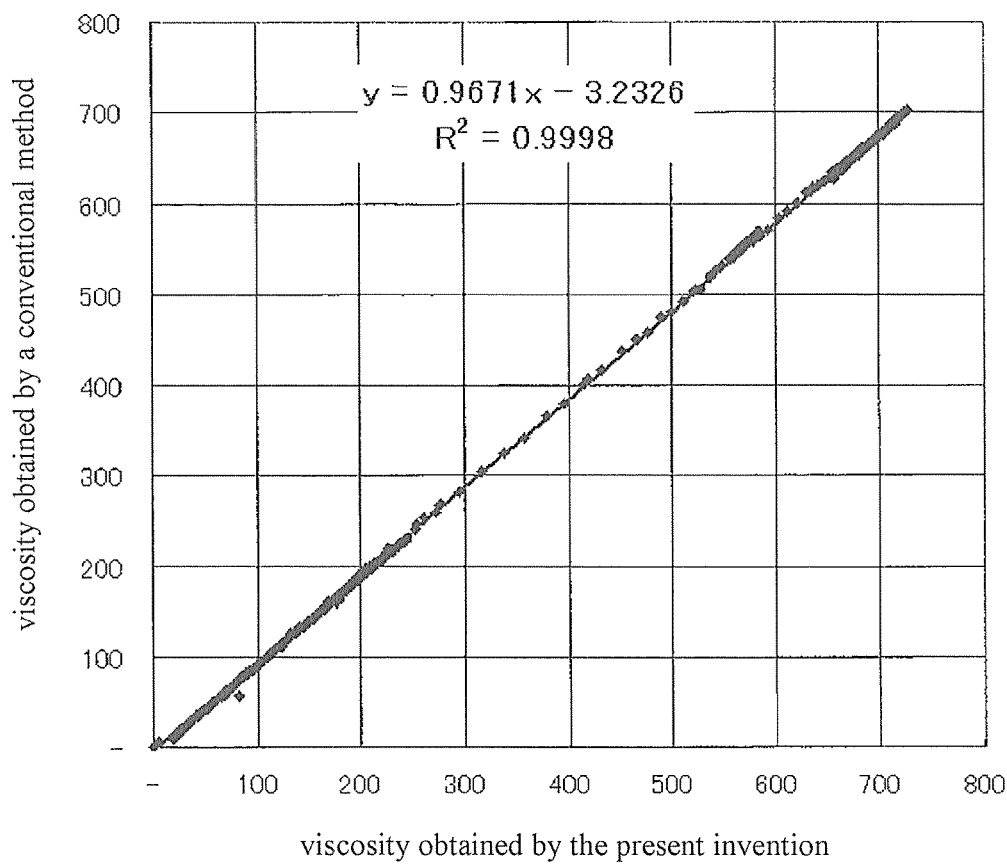
FIG. 8 is a graph illustrating the correlative analysis of the detected viscosity of reaction liquid by employing the present invention and the detected viscosity of reaction liquid by employing Patent reference 1.

The result of correlativity analysis of the viscosity of urethane resin detected in the example and the viscosity of urethane resin detected by the method of Patent reference 1 is shown in FIG. 8. Upon the collection of data, reactions of 3 to 4 batches are used. The linearity of the example is greater than the contribution ratio (the square of correlation coefficient) 0.999 and is extremely good.

Example 2

Fabrication of Polyester Resin

Instead of using diethylene glycol and toluene diisocyanate, polyethylene terephthalate resin is fabricated in the same manner as Example 1 by using terephthalic acid and ethylene glycol and a common method. As a result, according to the correlativity analysis of two viscosity values: viscosity of polyethylene terephthalate resin obtained by the method of present invention and viscosity of polyethylene terephthalate resin detected by the method of Patent reference 1, the correlation of the two viscosity values is very good and it is confirmed that polyester resin can be obtained by using the method of present invention.

Example 3

Fabrication of Acrylic Resin

Instead of using diethylene glycol and toluene diisocyanate, methyl methacrylate resin is fabricated in the same manner as Example 1 by using methyl methacrylate and a common method. As a result, according to the correlativity analysis of two viscosity values: the viscosity of methyl methacrylate resin obtained by the method of present invention and the viscosity of methyl methacrylate resin detected by the method of Patent reference 1, the correlation of the two viscosity values is very good and it is confirmed that methyl methacrylate resin can be obtained by using the method of present invention.

Example 4

Fabrication of Epoxy Resin

Instead of using diethylene glycol and toluene diisocyanate, epoxy resin is fabricated in the same manner as Example 1 by using epichlorohydrine and bisphenol A and a common method. As a result, according to the correlativity analysis of two viscosity values: viscosity of epoxy resin obtained by the method of present invention and viscosity of epoxy resin detected by the method of Patent reference 1, the correlation of the two viscosity values is very good and it is confirmed that epoxy resin can be obtained by using the method of present invention.

In light of the foregoing, embodiments and examples of the present invention are described, but the present invention is not limited thereto.

In addition, though the rotary speed shown in FIG. 4 is a second order approximation value, the rotary speed of the rotating shaft of the induction motor of the present invention can be determined as a third order or more than the third order approximation value, and the rotary torque and viscosity can also be determined based on the resulting rotary speed.

Furthermore, the to-be-detected object which is further detected by using the detected rotary speed (rotary torque) is not limited to be the viscosity of the reaction product and can also applied to other applications.

Description of Symbols 1 detection device
2 measurement unit
5 calculation processing unit
6 voltage lead-in wire
7 current lead-in wire
8 communication cable
9 induction motor
10 speed reducer
11 agitation shaft
12 reaction vessel
13 agitation blade
14 inverter
15 three-phase power source

What is claimed is:

1. A detection method of a rotary speed of a rotating shaft of an induction motor by using a calculation processing unit, wherein the detection method is that when a power input P is supplied to the induction motor, the rotary speed of the rotating shaft of the induction motor is detected, the detection method comprising:

a step I, comprising:
setting a loss power of when the power input P is supplied to the induction motor to be $P_L$, dividing the loss power $P_L$ into a loss power A that does not depend on the rotary speed of the rotating shaft of the induction motor and a loss power B that depends on the rotary speed;
considering a difference between the power input P and the loss power A as a first order approximation value $PM_1$ of mechanical output of the induction motor; and
from an equation $PM_1 = \alpha S_1$ ($\alpha$ is a motor constant) of an output $PM_1$ given in the induction motor and a slip $S_1$, obtaining a first order approximation value of the rotary speed of the rotating shaft $N_1 = N_S(1-S_1)$ ($N_S$ is a synchronous speed);

a step II, based on the first order approximation value $N_1$, obtaining the loss power $B_1$; and a step III, comprising:
considering a second order approximation value $PM_2$ of the output of the induction motor as $P-(A+B_1)$; and
from an equation $PM_2 = \alpha S_2$ ($\alpha$ is the motor constant) of the output $PM_2$ given in the induction motor and the slip $S_2$, obtaining a second order approximation value of the rotary speed of the rotating shaft, $N_2 = N_S(1-S_2)$ ($N_S$ is the synchronous speed)

wherein calculation of the step I, the step II and the step III is performed by the calculation processing unit.

2. The detection method of a rotary speed of a rotating shaft of an induction motor according to claim 1, further comprising repeating a step IV and a step V for a predetermined number of times after the second order approximation value $N_2$ is obtained by the step III, wherein the step IV is obtaining a loss power $B_n$ based on an $n^{th}$ order approximation value $N_n$;

the step V comprising:
considering a $(n+1)^{th}$ order approximation value $PM_{(n+1)}$ of the output of the induction motor as $P-(A+B_n)$; and
from an equation $PM_{(n+1)} = \alpha S_{(n+1)}$ ($\alpha$ is the motor constant) of the output $PM_{(n+1)}$ given in the induction motor and the slip $S_{(n+1)}$, obtaining a $(n+1)^{th}$ order approximation value of the rotary speed of the rotating shaft, $N_{(n+1)} = N_S(1-S_{(n+1)})$ ($N_S$ is the synchronous speed, n is an integer equal to or greater than 2).

3. A device for detecting a rotary speed of a rotating shaft of an induction motor, wherein the device detects the rotary speed of the rotating shaft of the induction motor when a power input P is supplied to the induction motor, the device comprising:

an information obtaining unit for obtaining a measurement information including a power input P, a current, a voltage and a voltage frequency supplied to the induction motor; and a calculation processing unit for obtaining the rotary speed of the rotating shaft of the induction motor by calculation based on the measurement information, wherein the calculation processing unit performs a process defined in a detection method of the rotary speed of the rotating shaft of the induction motor, wherein the detection method comprising:

a step I, comprising:
setting a loss power of when the power input P is supplied to the induction motor to be $P_L$, dividing the loss power $P_L$ into a loss power A that does not depend on the rotary speed of the rotating shaft of the induction motor and a loss power B that depends on the rotary speed;
considering a difference between the power input P and the loss power A as a first order approximation value $PM_1$ of mechanical output of the induction motor; and
from an equation $PM_1 = \alpha S_1$ ($\alpha$ is a motor constant) of an output $PM_1$ given in the induction motor and a slip $S_1$, obtaining a first order approximation value of the rotary speed of the rotating shaft $N_1 = N_S(1-S_1)$ ($N_S$ is a synchronous speed);

a step II, based on the first order approximation value $N_1$, obtaining the loss power $B_1$; and a step III, comprising:
considering a second order approximation value $PM_2$ of the output of the induction motor as $P-(A+B_1)$; and
from an equation $PM_2 = \alpha S_2$ ($\alpha$ is the motor constant) of the output $PM_2$ given in the induction motor and the slip $S_2$, obtaining a second order approximation value of the rotary speed of the rotating shaft, $N_2 = N_s(1-S_2)$ ($N_s$ is the synchronous speed).

4. The device for detecting a rotary speed of a rotating shaft of an induction motor according to claim 3, wherein the calculation processing unit further repeating a step IV and a step V for a predetermined number of times after the second order approximation value $N_2$ is obtained by the step III, wherein the step IV is obtaining a loss power $B_n$ based on an $n^{th}$ order approximation value $N_n$;

the step V comprising:
considering a $(n+1)^{th}$ order approximation value $PM_{(n+1)}$ of the output of the induction motor as $P-(A+B_n)$; and
from an equation $PM_{(n+1)} = \alpha S_{(n+1)}$ ($\alpha$ is the motor constant) of the output $PM_{(n+1)}$ given in the induction motor and the slip $S_{(n+1)}$, obtaining a $(n+1)^{th}$ order approximation value of the rotary speed of the rotating shaft, $N_{(n+1)} = N_S(1-S_{(n+1)})$ ($N_S$ is the synchronous speed, n is an integer equal to or greater than 2).

5. A detection method of a rotary torque of a rotating shaft of an induction motor by using a calculation processing unit, wherein the detection method is that when a power input P is supplied to the induction motor, the rotary torque of the rotating shaft of the induction motor is detected, the detection method comprising:

a step I, comprising:
setting a loss power of when the power input P is supplied to the induction motor to be $P_L$, dividing the loss power $P_L$ into a loss power A that does not depend on the rotary speed of the rotating shaft of the induction motor and a loss power B that depends on the rotary speed;
considering a difference between the power input P and the loss power A as a first order approximation value $PM_1$ of mechanical output of the induction motor; and
from an equation $PM_1 = \alpha S_1$ ($\alpha$ is a motor constant) of an output $PM_1$ given in the induction motor and a slip $S_1$, obtaining a first order approximation value of the rotary speed of the rotating shaft $N_1 = N_S(1-S_1)$ ($N_S$ is a synchronous speed);

a step II, based on the first order approximation value $N_1$, obtaining the loss power $B_1$; and a step III, comprising:
considering a second order approximation value $PM_2$ of the output of the induction motor as $P-(A+B_1)$; and
from an equation $PM_2=\alpha S_2$ ($\alpha$ is the motor constant) of the output $PM_2$ given in the induction motor and the slip $S_2$, obtaining a second order approximation value of the rotary speed of the rotating shaft, $N_2 = N_S(1-S_2)$ ($N_S$ is the synchronous speed);
based on the loss power A, the loss power $B_1$ obtained from the step II, and the second order approximation value of the rotary speed $N_2$ obtained from the step III, obtaining the rotary torque T by using an equation $$T=(P-(A+B_1))/(2\pi \times N_2/60),$$

wherein calculation of the step I, the step II, the step III and the equation used for obtaining the rotary torque T is performed by the calculation processing unit.

6. A device for detecting a rotary torque of a rotating shaft of an induction motor, wherein the device detects the rotary torque of the rotating shaft of the induction motor when a power input P is supplied to the induction motor, the device comprising:
an information obtaining unit for obtaining a measurement information including a power input P, a current, a voltage and a voltage frequency supplied to the induction motor; and
a calculation processing unit for obtaining the rotary torque of the rotating shaft of the induction motor by calculation based on the measurement information,
wherein the calculation processing unit performs a process defined in a detection method of the rotary speed of the rotating shaft of the induction motor, wherein the detection method comprising:
a step I, comprising:
setting a loss power of when the power input P is supplied to the induction motor to be $P_L$, dividing the loss power $P_L$ into a loss power A that does not depend on the rotary speed of the rotating shaft of the induction motor and a loss power B that depends on the rotary speed;
considering a difference between the power input P and the loss power A as a first order approximation value $PM_1$ of mechanical output of the induction motor; and
from an equation $PM_1=\alpha S_1$ ($\alpha$ is a motor constant) of an output $PM_1$ given in the induction motor and a slip $S_1$, obtaining a first order approximation value of the rotary speed of the rotating shaft $N_1=N_s(1-S_1)$ ($N_s$ is a synchronous speed);
a step II, based on the first order approximation value $N_1$, obtaining the loss power $B_1$; and
a step III, comprising:
considering a second order approximation value $PM_2$ of the output of the induction motor as $P-(A+B_1)$; and
from an equation $PM_2=\alpha S_2$ ($\alpha$ is the motor constant) of the output $PM_2$ given in the induction motor and the slip $S_2$, obtaining a second order approximation value of the rotary speed of the rotating shaft, $N_2=N_S(1-S_2)$ ($N_S$ is the synchronous speed); and
performs a calculation, based on the loss power A, the loss power $B_1$ obtained from the step II, and the second order approximation value of the rotary speed $N_2$, obtained from the step III, by using an equation $$T=(P-(A+B_1))/(2\pi \times N_2/60).$$

7. A detection method of a viscosity of a reaction liquid by using a calculation processing unit, wherein the detection method is to detect he viscosity of the reaction liquid when the reaction liquid is agitated by a rotation of a rotating shaft having an agitation blade of an induction motor which serves as a power source, the detection method comprising:
a detection method of the rotary speed of the rotating shaft of the induction motor, wherein the detection method of the rotary speed comprising:
a step I, comprising:
setting a loss power of when a power input P is supplied to the induction motor to be $P_L$, dividing the loss power $P_L$ into a loss power A that does not depend on the rotary speed of the rotating shaft of the induction motor and a loss power B that depends on the rotary speed;
considering a difference between the power input P and the loss power A as a first order approximation value $PM_1$ of mechanical output of the induction motor; and
from an equation $PM_1=\alpha S_1$ ($\alpha$ is a motor constant) of an output $PM_1$ given in the induction motor and a slip $S_1$, obtaining a first order approximation value of the rotary speed of the rotating shaft $N_1=N_s(1-S_1)$ ($N_s$ is a synchronous speed);
a step II, based on the first order approximation value $N_1$, obtaining the loss power $B_1$; and
a step III, comprising:
considering a second order approximation value $PM_2$ of the output of the induction motor as $P-(A+B_1)$; and
from an equation $PM_2=\alpha S_2$ ($\alpha$ is the motor constant) of the output $PM_2$ given in the induction motor and the slip $S_2$, obtaining a second order approximation value of the rotary speed of the rotating shaft, $N_2=N_s(1-S_2)$ ($N_s$ is the synchronous speed);
obtaining a rotary torque T of the rotating shaft by using an equation
$T=(P-(A+B_1))/(2\pi \times N_2/60),$ based on the loss power A, the loss power $B_1$ obtained from the step II, and the second order approximation value of the rotary speed $N_2$ obtained from the step III; and
from the rotary torque T, obtaining the viscosity $\eta$ by using an equation
$\eta = \kappa T/N$ (unit Pa·S) ($\kappa$ is a constant determined according to dimensions of the agitation blade and a reaction vessel used to agitate the reaction liquid),
wherein calculation of the step I, the step II the step III, the equation used for obtaining the rotary torque T, and the equation used for obtaining the viscosity $\eta$ is performed by the calculation processing unit.

8. A device for detecting a viscosity of a reaction liquid, wherein the device is disposed in a reaction vessel that agitates the reaction liquid by a rotation of a rotating shaft having an agitation blade of an induction motor which serves as a power source, the device comprising:
an information obtaining unit for obtaining a measurement information including a power input P, a current, a voltage and a voltage frequency supplied to the induction motor; and
a calculation processing unit for obtaining the viscosity of the reaction liquid based on the measurement information,
wherein the calculation processing unit performs a process defined in a detection method of the rotary speed of the rotating shaft of the induction motor, wherein the detection method comprising:
a step I, comprising:
setting a loss power of when the power input P is supplied to the induction motor to be $P_L$, dividing the loss power $P_L$ into a loss power A that does not depend on the rotary speed of the rotating shaft of the induction motor and a loss power B that depends on the rotary speed;

considering a difference between the power input P and the loss power A as a first order approximation value $PM_1$ of mechanical output of the induction motor; and from an equation $PM_1 = \alpha S_1$ ($\alpha$ is a motor constant) of an output $PM_1$ given in the induction motor and a slip $S_1$, obtaining a first order approximation value of the rotary speed of the rotating shaft $N_1 = N_S(1-S_1)$ ($N_S$ is a synchronous speed);

a step II, based on the first order approximation value $N_1$, obtaining the loss power $B_1$; and a step III, comprising:

considering a second order approximation value $PM_2$ of the output of the induction motor as $P-(A+B_1)$; and from an equation $PM_2 = \alpha S_2$ ($\alpha$ is the motor constant) of the output $PM_2$ given in the induction motor and the slip $S_2$, obtaining a second order approximation value of the rotary speed of the rotating shaft, $N_2 = N_s(1-S_2)$ ($N_s$ is the synchronous speed); and performs a calculation, based on the loss power A, the loss power $B_1$ obtained from the step II, and the second order approximation value of the rotary speed $N_2$ obtained from the step III, by using an equation $T=(P-(A+B_1))/(2\pi \times N_2/60)$ to obtain a rotary torque T, and from the obtained rotary torque T the calculation processing unit performs a calculation of the viscosity $\eta$ by using an equation $\eta = \kappa T/N$ (unit Pa·S) ($\kappa$ is a constant determined according to dimensions of the agitation blade and a reaction vessel used to agitate the reaction liquid).

9. A manufacturing method of a reaction product, wherein at least one kind of compound is used as a raw material, and in a reaction process of producing the raw material, the reaction product whose viscosity varies with the reaction process is manufactured, and the reaction is performed inside a reaction vessel which agitates the reaction product by a rotation of a rotating shaft having an agitation blade of an induction motor which is used as a power source, during the reaction, the manufacturing method comprising:

a first process, detecting a rotary speed of the rotating shaft of the induction motor by using a method for detecting the rotary speed, comprising:

a step I, comprising:

setting a loss power of when a power input P is supplied to the induction motor to be $P_L$, and dividing the loss power $P_L$ into a loss power A which does not depend on the rotary speed of the rotating shaft of the induction motor and a loss power B which depends on the rotary speed;

considering a difference between the power input P and the loss power A as a first order approximation value of mechanical output of the induction motor $PM_1$; and from an equation $PM_1 = \alpha S_1$ ($\alpha$ is a motor constant) of an output $PM_1$ given in the induction motor and a slip $S_1$, obtaining a first order approximation value of the rotary speed of the rotating shaft, $N_1 = N_S(1-S_1)$ ($N_S$ is a synchronous speed);

a step II, based on the first order approximation value $N_1$, obtaining the loss power $B_1$; and a step III, comprising:

considering a second order approximation value $PM_2$ of the output of the induction motor as $P-(A+B_1)$; and from an equation $PM_2 = \alpha S_2$ ($\alpha$ is the motor constant) of the output $PM_2$ given in the induction motor and the slip $S_2$, obtaining a second order approximation value of the rotary speed of the rotating shaft, $N_2 = N_S(1-S_2)$ ($N_S$ is the synchronous speed);

a second process, detecting a rotary torque of the rotating shaft of the induction motor by using a method for detecting the rotary torque, comprising:

obtaining a rotary torque T by using an equation $T=(P-(A+B_1))/(2\pi \times N_2/60)$, based on the loss power A, the loss power $B_1$ obtained from the step II, and the second order approximation value $N_2$ of the rotary speed obtained from the step III; and a third process, obtaining a viscosity of the reaction product, comprising:

from the rotary torque T obtained by a detecting process of the rotary speed, obtaining the viscosity $\eta$ by using an equation $\eta = \kappa T/N$ (unit Pa·S) ($\kappa$ is a constant determined according to dimensions of the agitation blade and a reaction vessel used to agitate the reaction liquid).

10. The manufacturing method of a reaction product according to claim 9, wherein the reaction product is a resin.

11. The manufacturing method of a reaction product according to claim 10, wherein the resin is one or more kinds of resin selected from the group consisting of an epoxy resin, a polyurethane resin, a polyester resin and an acrylic resin.

* * * * *